US012629264B2

(12) United States Patent
Caratsch

(10) Patent No.: US 12,629,264 B2
(45) Date of Patent: May 19, 2026

(54) EXPANDABLE AND MODULAR INTERVERTEBRAL IMPLANT

(71) Applicant: Alexander Caratsch, Trelex (CH)

(72) Inventor: Alexander Caratsch, Trelex (CH)

(73) Assignee: Alexander Caratsch, Trelex (CH)

( * ) Notice: Subject to any disclaimer, the term of this patent is extended or adjusted under 35 U.S.C. 154(b) by 549 days.

(21) Appl. No.: 18/245,412

(22) PCT Filed: Sep. 21, 2021

(86) PCT No.: PCT/CH2021/050021
§ 371 (c)(1),
(2) Date: Mar. 15, 2023

(87) PCT Pub. No.: WO2022/061477
PCT Pub. Date: Mar. 31, 2022

(65) Prior Publication Data
US 2023/0270561 A1      Aug. 31, 2023

(30) Foreign Application Priority Data

| Sep. 23, 2020 | (CH) | ....................................... | 1211/20 |
| May 2, 2021 | (CH) | ....................................... | 476/21 |
| Jun. 1, 2021 | (CH) | ....................................... | 639/21 |
| Jun. 18, 2021 | (CH) | ....................................... | 716/21 |
| Aug. 4, 2021 | (CH) | ............................... | 70136/2021 |
| Aug. 10, 2021 | (CH) | ................................ | 70155/2021 |

(51) Int. Cl.
| A61F 2/44 | (2006.01) |
| A61F 2/28 | (2006.01) |
| A61F 2/46 | (2006.01) |

(52) U.S. Cl.
CPC .................. *A61F 2/46* (2013.01); *A61F 2/28* (2013.01); *A61F 2/4455* (2013.01); *A61F 2002/2835* (2013.01)

(58) Field of Classification Search
CPC ..... A61F 2/4611; A61B 2/442; A61B 2/4425; A61B 2002/443; A61B 2002/4455
USPC ........................................... 623/17.11–17.16
See application file for complete search history.

(56) References Cited

U.S. PATENT DOCUMENTS

| 6,126,689 | A | * | 10/2000 | Brett | ..................... | A61F 2/4455 623/17.15 |
| 6,395,031 | B1 | | 5/2002 | Foley et al. | | |
| 7,318,839 | B2 | | 1/2008 | Malberg et al. | | |
| 7,731,751 | B2 | | 6/2010 | Butler et al. | | |

(Continued)

FOREIGN PATENT DOCUMENTS

EP          1645248 B1          9/2009

*Primary Examiner* — Eduardo C Robert
*Assistant Examiner* — Christina NegrelliRodriguez
(74) *Attorney, Agent, or Firm* — Girma Wolde-Michael

(57) ABSTRACT

An interbody cage for the spinal column structured as a scaffold made of at least two folding and unfolding scaffoldings: one base member (also named a cage body) which receives the pivoting means of a pivoting member (also named an extension member), and one extension member, structured to pivot around an axis on the cage body from a first folded or stowed configuration to a second unfolded or deployed configuration such that the perimeters of the contact surfaces between the interbody cage and the vertebrae and/or the height of the interbody cage increase from the stowed configuration to the deployed configuration.

14 Claims, 21 Drawing Sheets

(56) References Cited

U.S. PATENT DOCUMENTS

| | | | |
|---|---|---|---|
| 8,034,109 B2 | 10/2011 | Zwirkoski | |
| 8,187,332 B2 | 5/2012 | McLuen | |
| 8,795,368 B2 | 8/2014 | Trieu et al. | |
| 9,289,314 B2 | 3/2016 | Perisic | |
| 9,433,510 B2 | 9/2016 | Lechmann et al. | |
| 9,452,064 B2 | 9/2016 | Trautwein et al. | |
| 9,480,573 B2 | 11/2016 | Perloff et al. | |
| 9,707,095 B2 | 7/2017 | Emstad | |
| 9,795,493 B1 | 10/2017 | Bannigan | |
| 10,265,187 B2 | 4/2019 | Zipnick | |
| 10,383,743 B2 | 8/2019 | To et al. | |
| 10,575,966 B2 | 3/2020 | Logan et al. | |
| 10,898,340 B2 | 1/2021 | Koch et al. | |
| 11,234,834 B2 | 2/2022 | Caratsch | |
| 11,497,619 B2 * | 11/2022 | Flower | A61L 27/32 |
| 2006/0142859 A1 * | 6/2006 | McLuen | A61F 2/4455 |
| | | | 623/17.11 |
| 2010/0010633 A1 | 1/2010 | Kohm | |
| 2011/0208311 A1 * | 8/2011 | Janowski | A61F 2/4425 |
| | | | 623/17.16 |
| 2011/0276141 A1 | 11/2011 | Caratsch | |
| 2012/0109319 A1 | 5/2012 | Perisic | |
| 2012/0303124 A1 * | 11/2012 | McLuen | A61F 2/4455 |
| | | | 623/17.16 |
| 2013/0069302 A1 | 3/2013 | Naoi | |
| 2013/0197647 A1 * | 8/2013 | Wolters | A61F 2/442 |
| | | | 623/17.16 |
| 2016/0045328 A1 * | 2/2016 | Matthews | A61F 2/4455 |
| | | | 623/17.16 |
| 2017/0216051 A1 | 8/2017 | Dewey | |
| 2019/0307577 A1 | 10/2019 | Predick et al. | |
| 2019/0336299 A1 | 11/2019 | Bernard et al. | |
| 2020/0281739 A1 | 9/2020 | Jimenez et al. | |

* cited by examiner

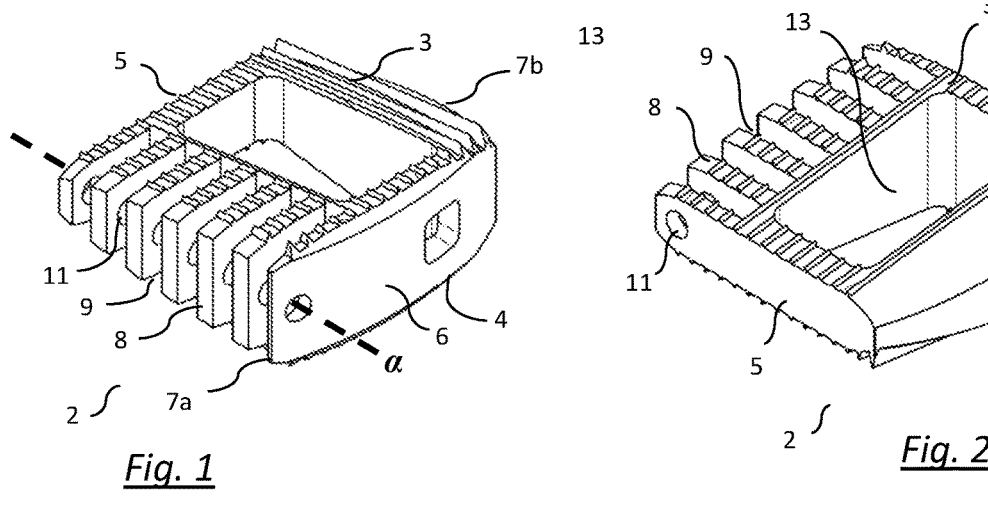
_Fig. 1_
_Fig. 2_
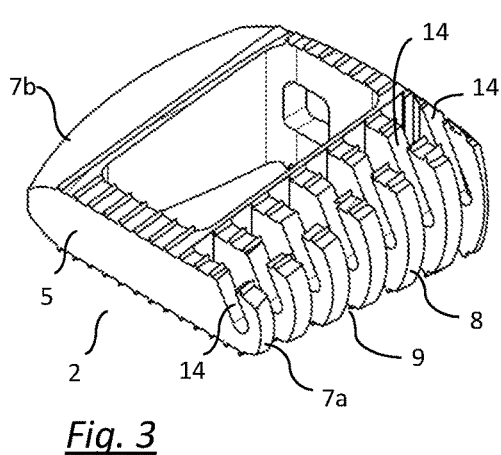
_Fig. 3_
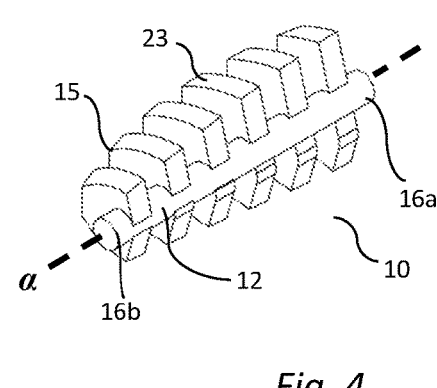
_Fig. 4_
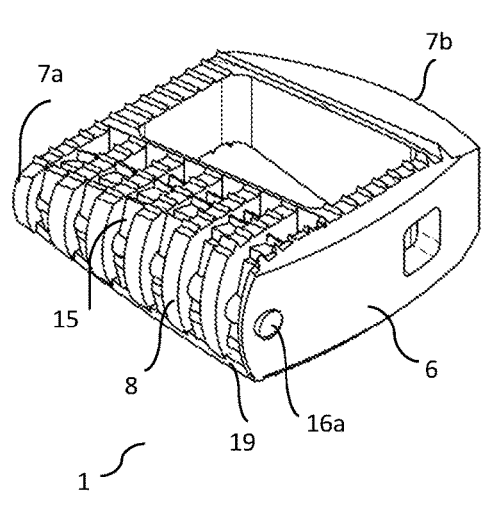
_Fig. 5_
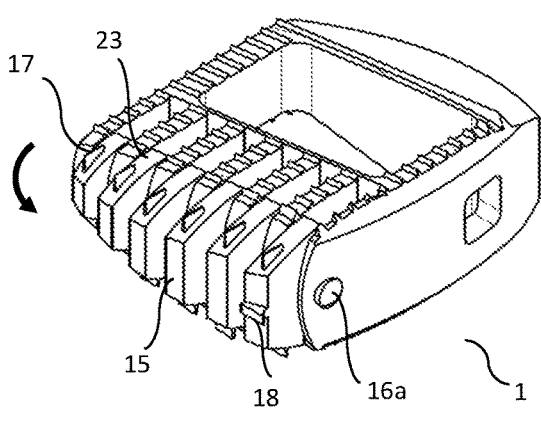
_Fig. 6_

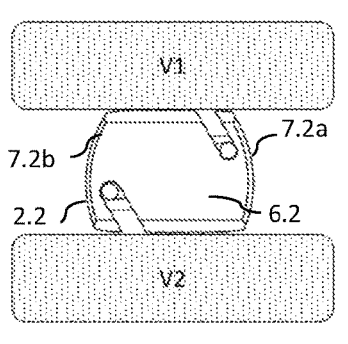
_Fig. 18a_
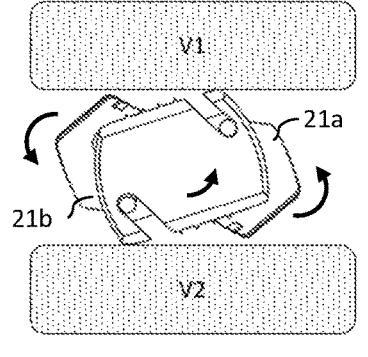
_Fig. 18b_
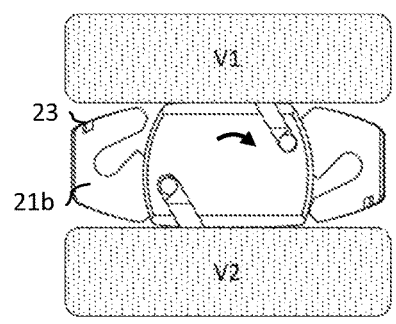
_Fig. 18c_
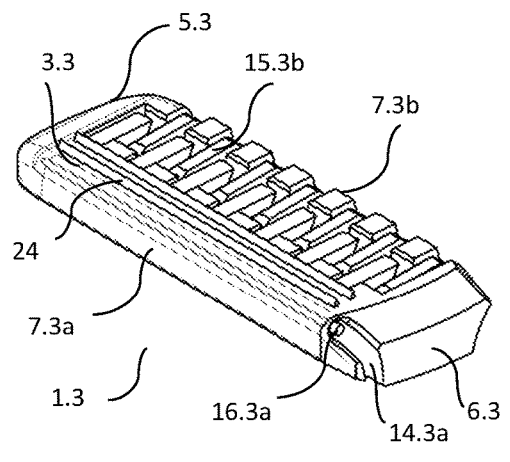
_Fig. 19_
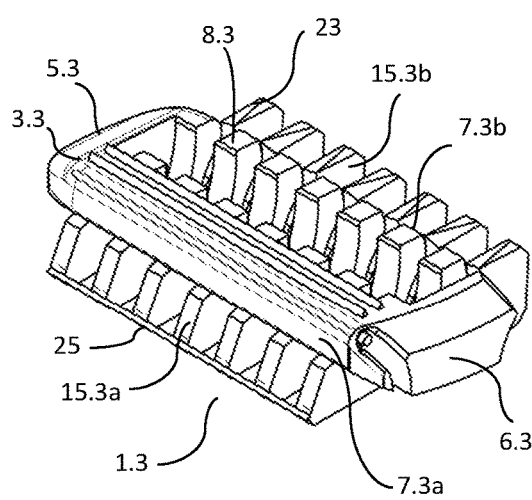
_Fig. 20_
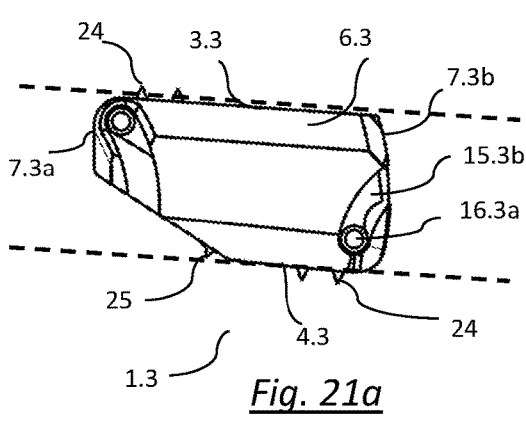
_Fig. 21a_
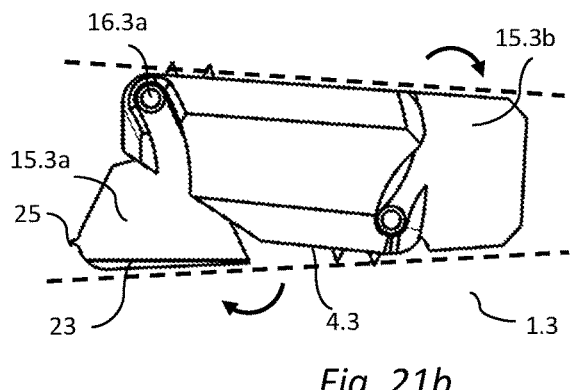
_Fig. 21b_

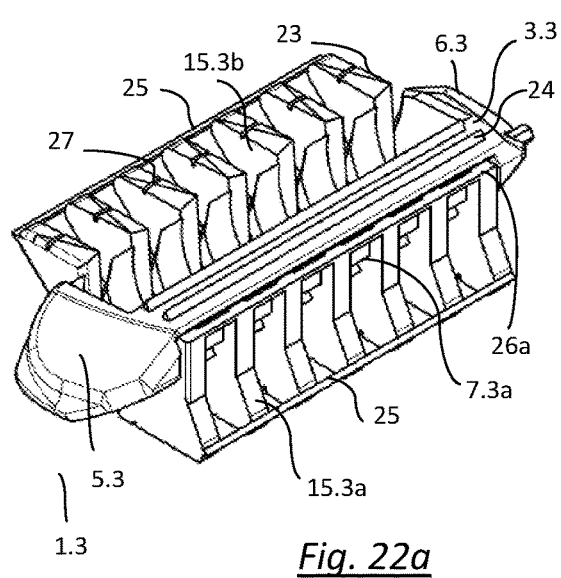
*Fig. 22a*
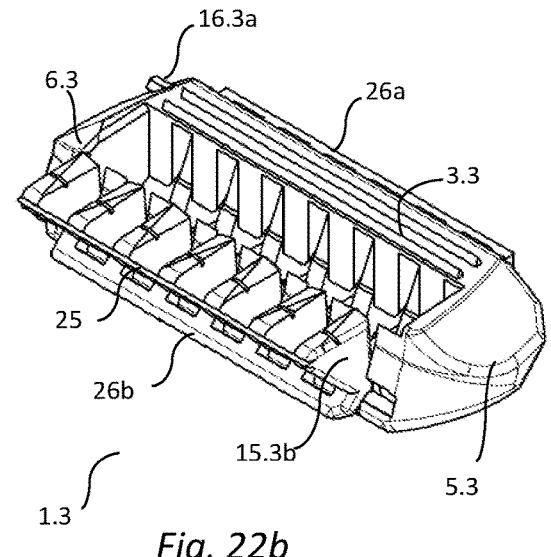
*Fig. 22b*
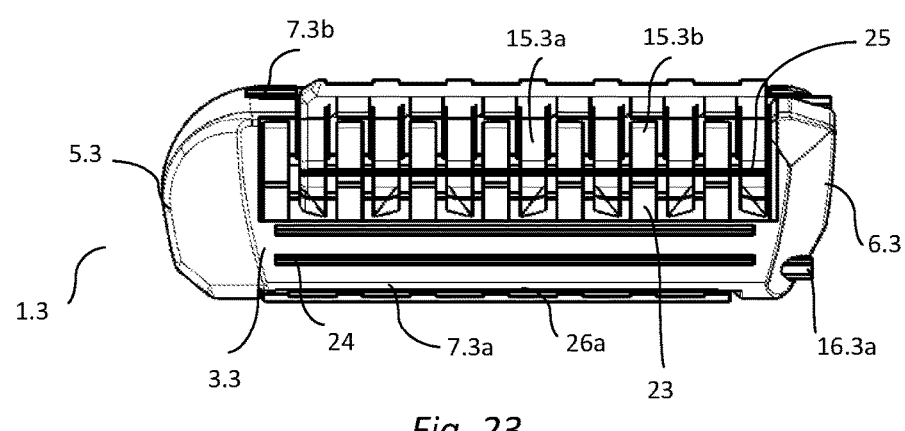
*Fig. 23*
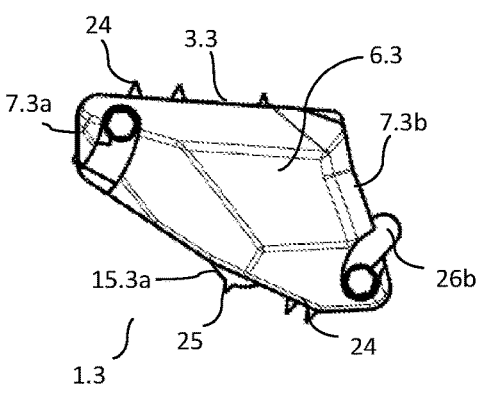
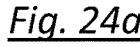
*Fig. 24a*
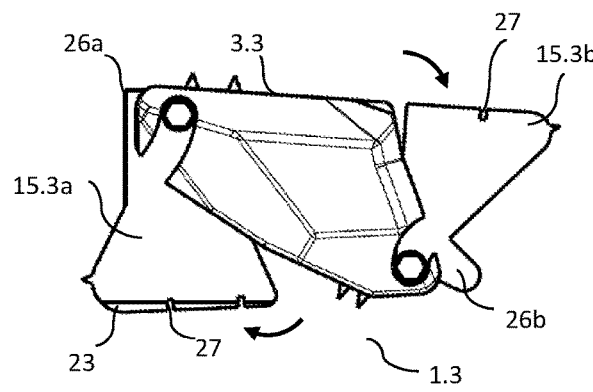
*Fig. 24b*

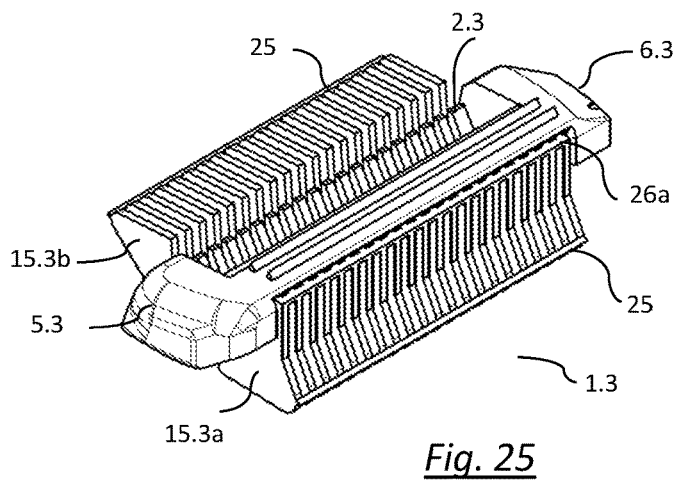
*Fig. 25*
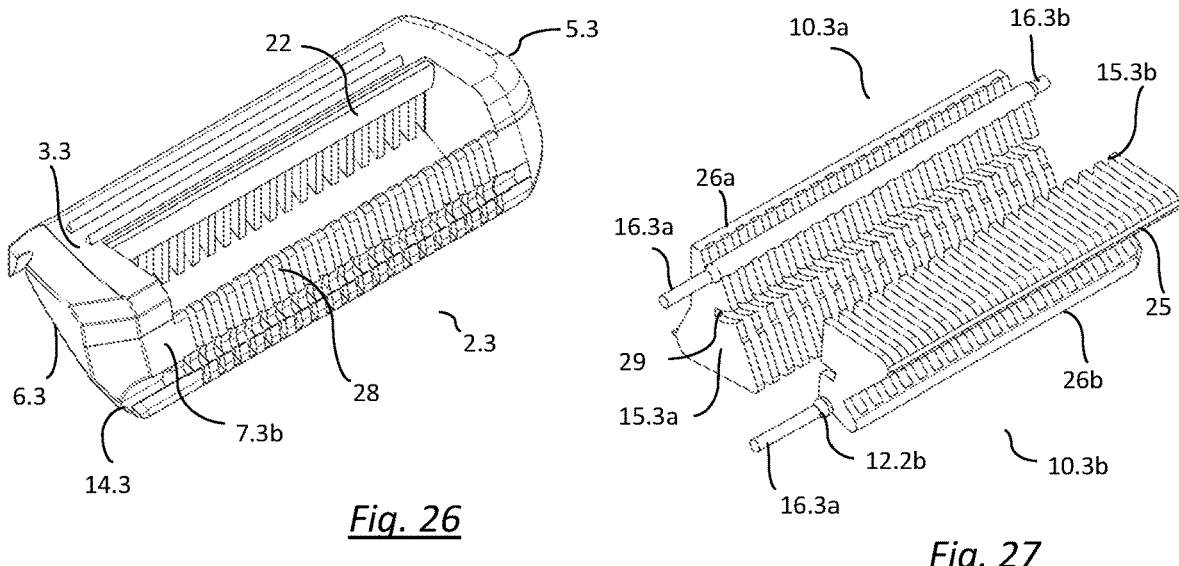
*Fig. 26*
*Fig. 27*
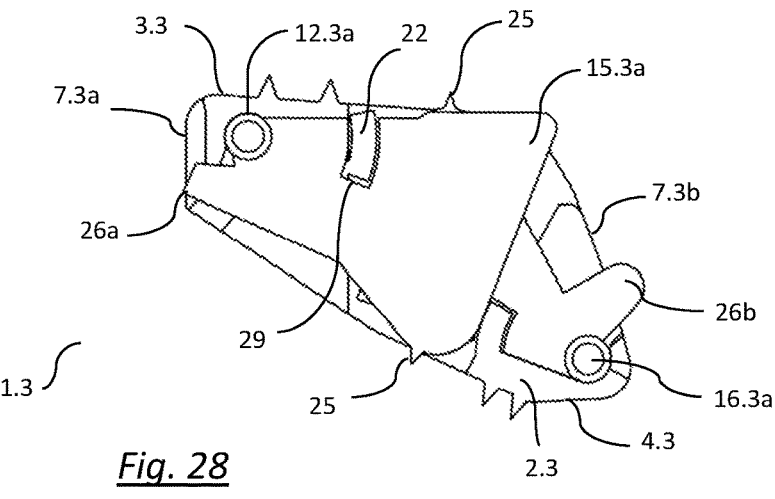
*Fig. 28*

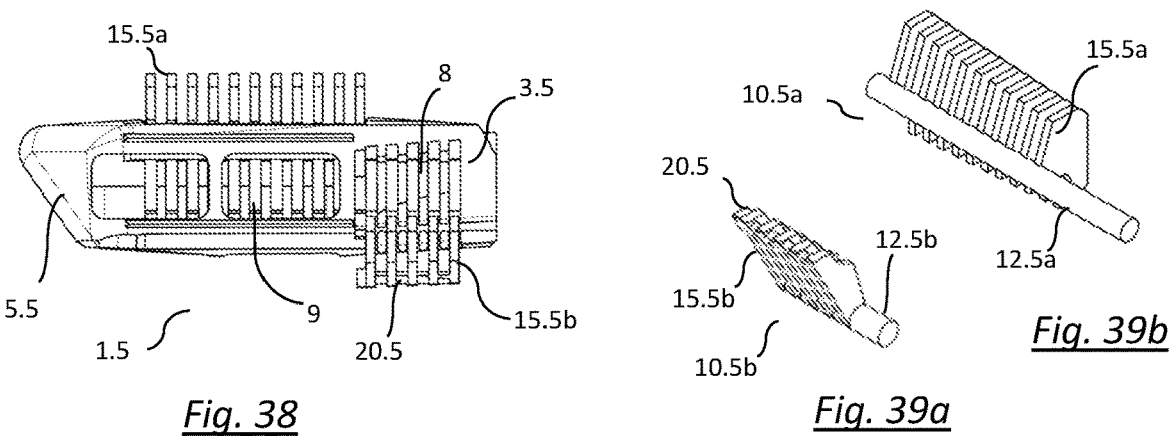
Fig. 38
Fig. 39b
Fig. 39a
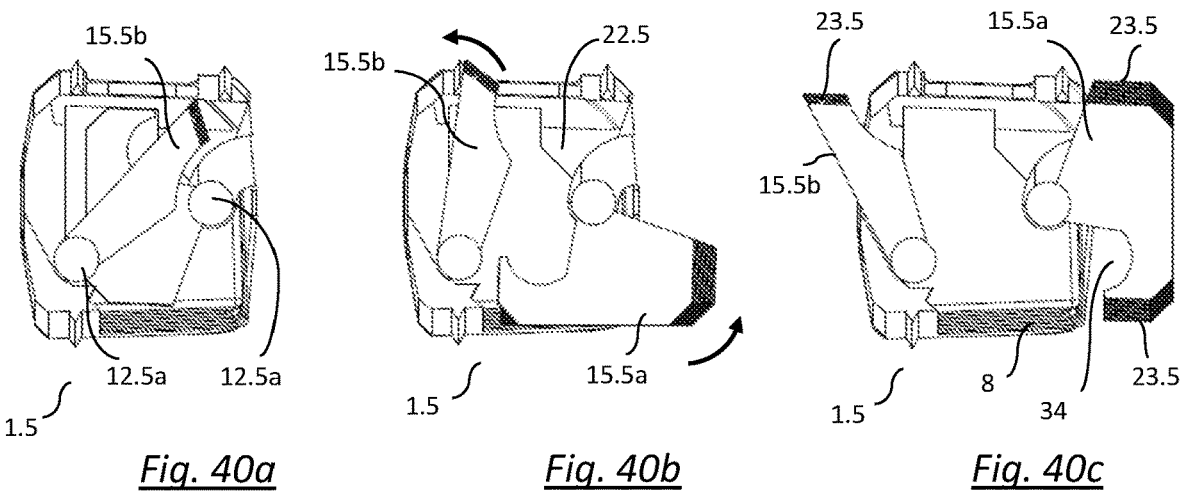
Fig. 40a
Fig. 40b
Fig. 40c
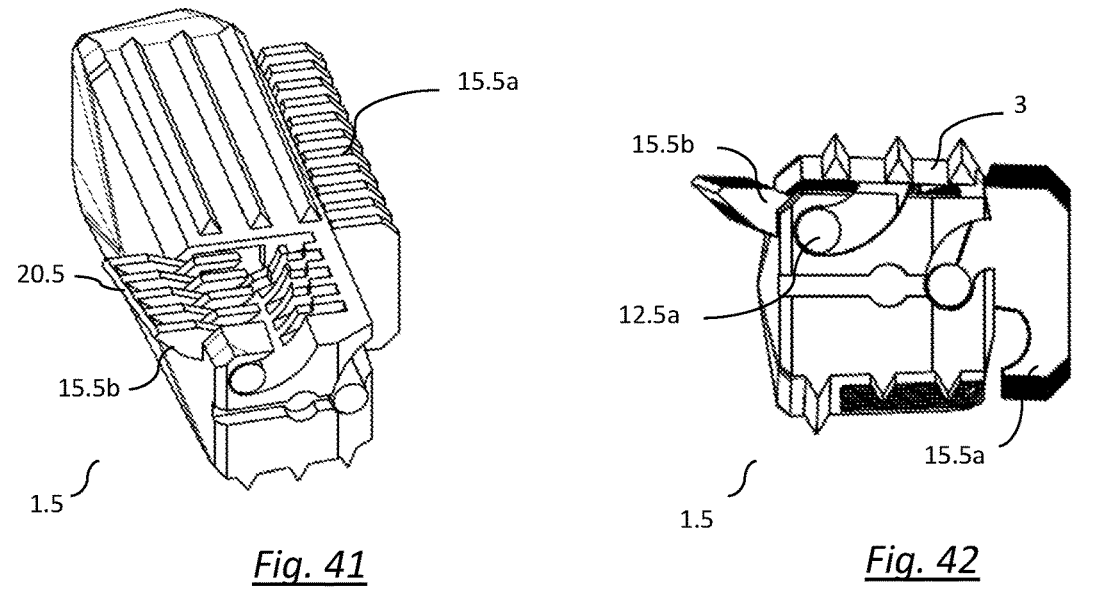
Fig. 41
Fig. 42

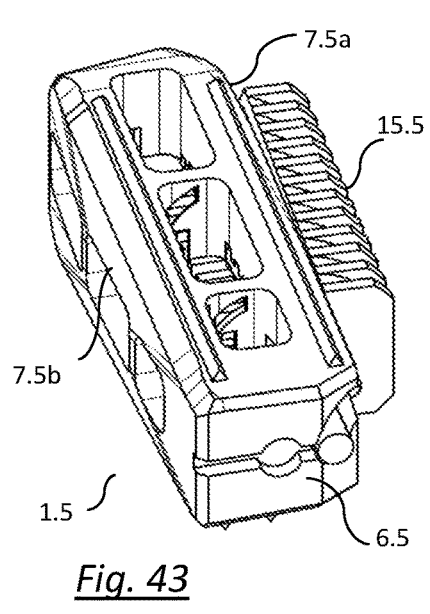
Fig. 43
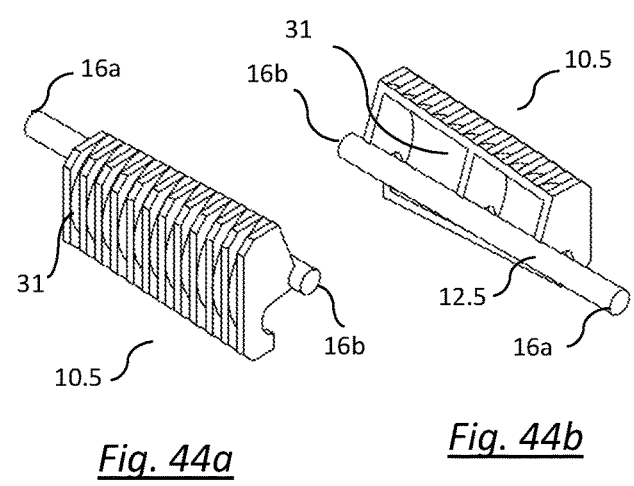
Fig. 44a
Fig. 44b
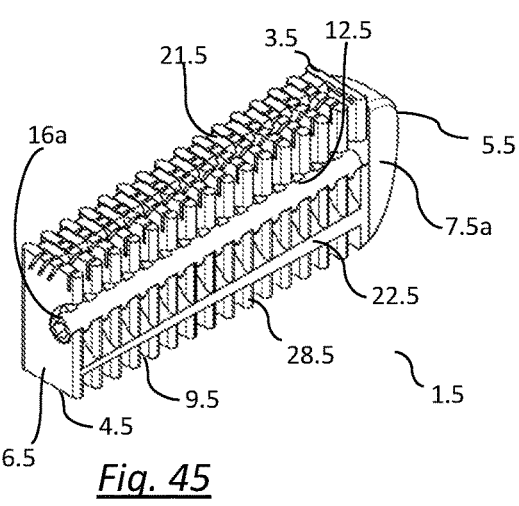
Fig. 45
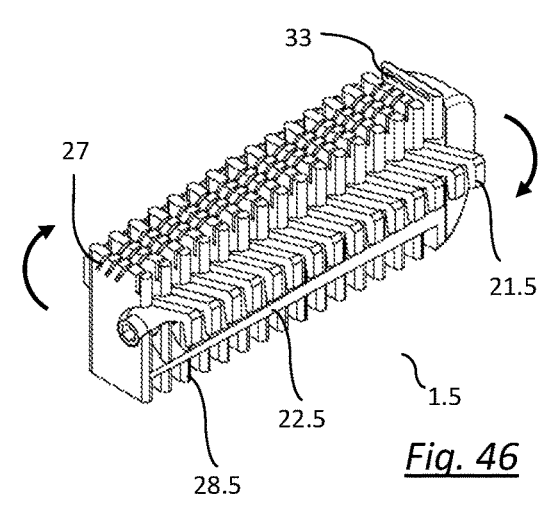
Fig. 46
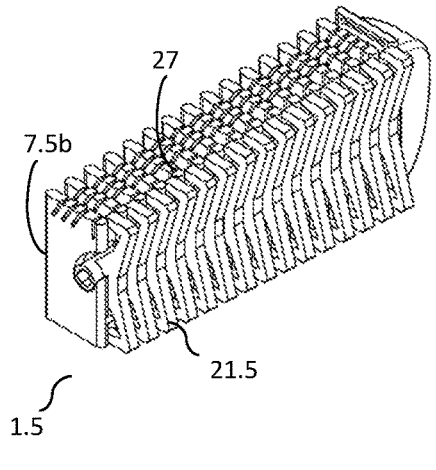
Fig. 47
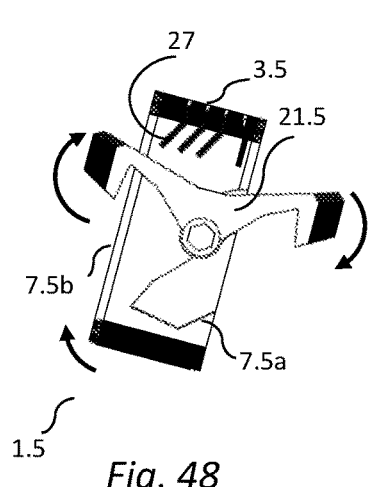
Fig. 48
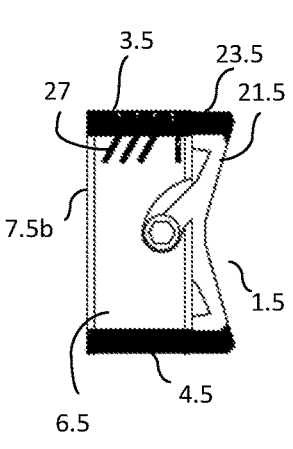
Fig. 49

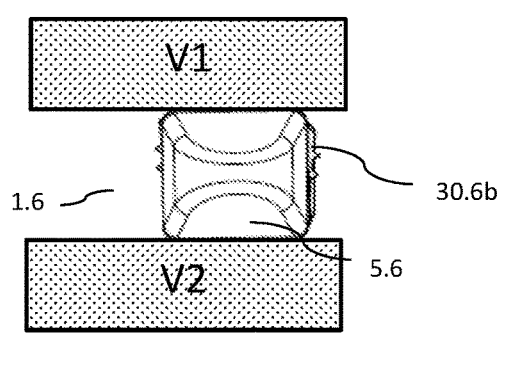
*Fig. 55a*
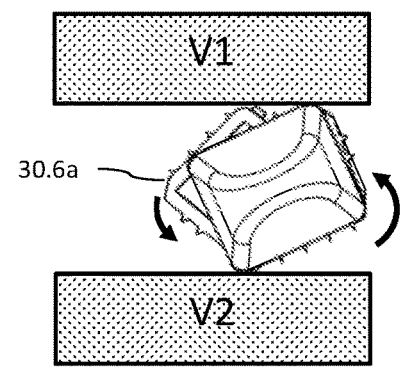
*Fig. 55b*
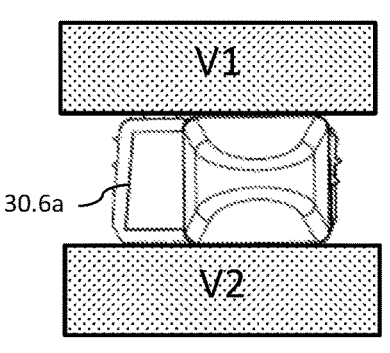
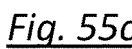
*Fig. 55c*
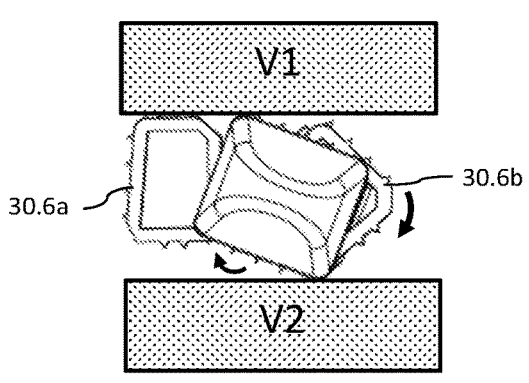
*Fig. 55d*
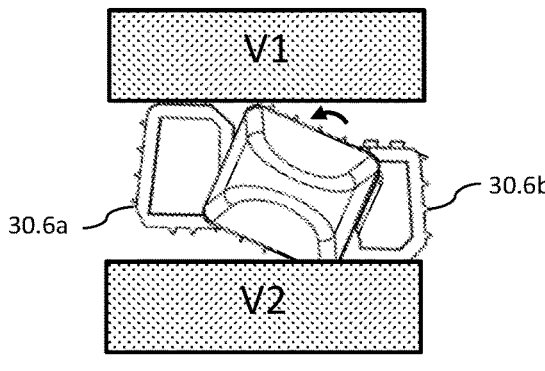
*Fig. 55e*
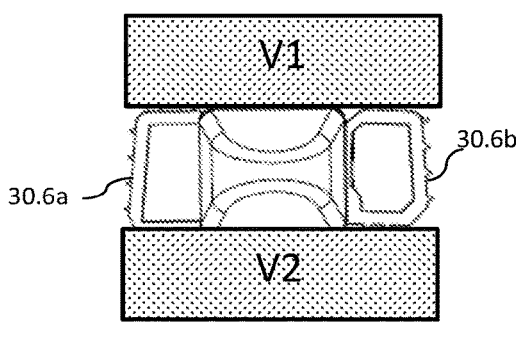
*Fig. 55f*

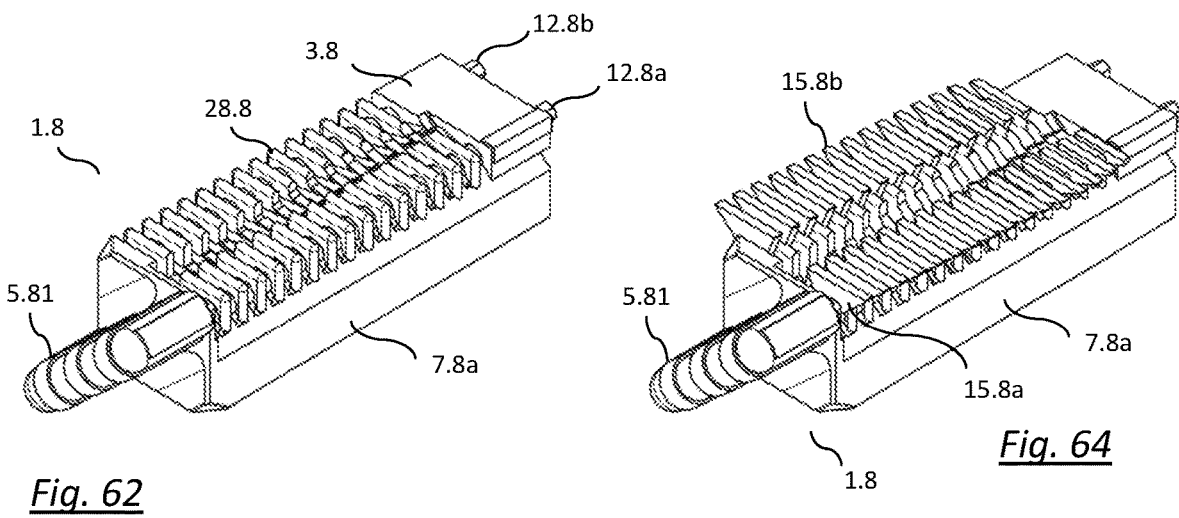
*Fig. 62*
*Fig. 64*
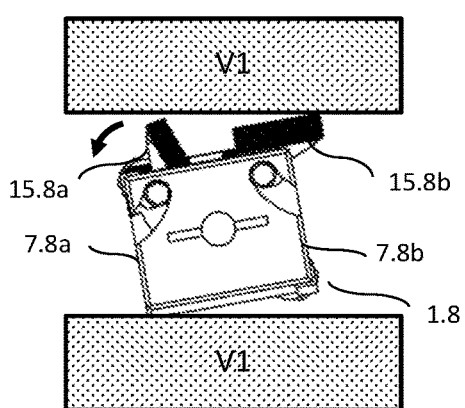
*Fig. 63*
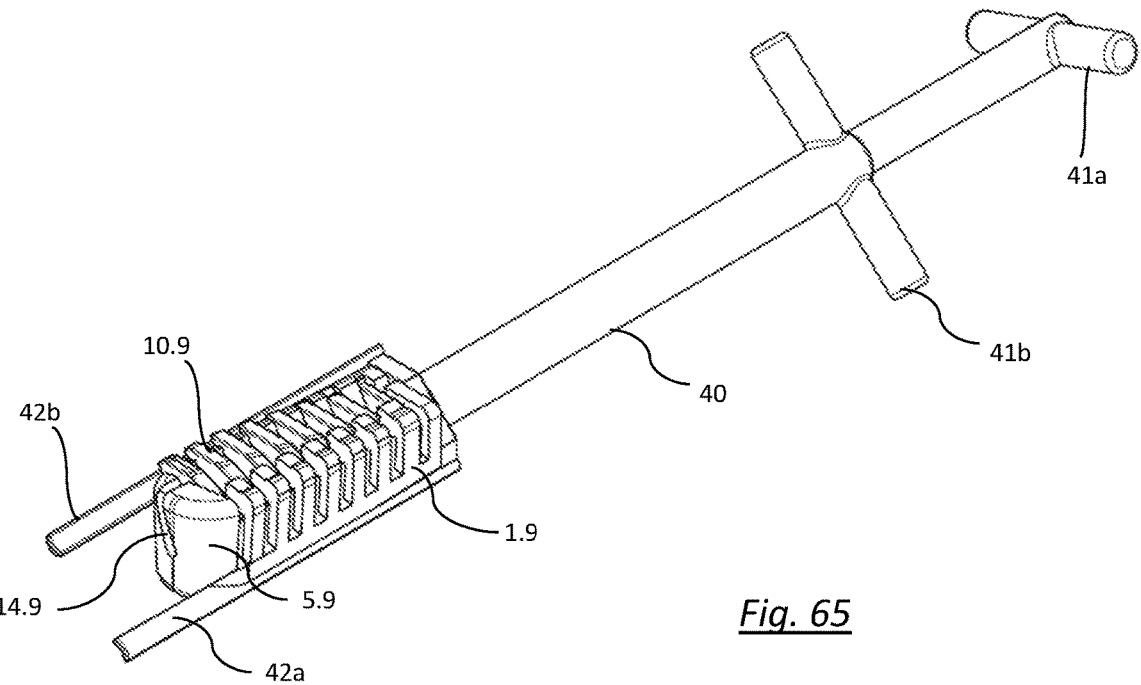
*Fig. 65*

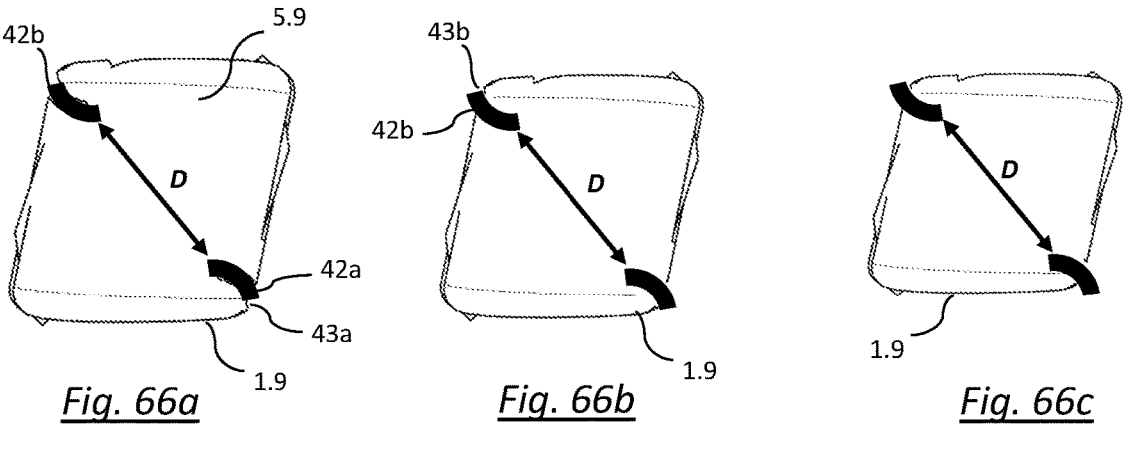
*Fig. 66a*     *Fig. 66b*     *Fig. 66c*
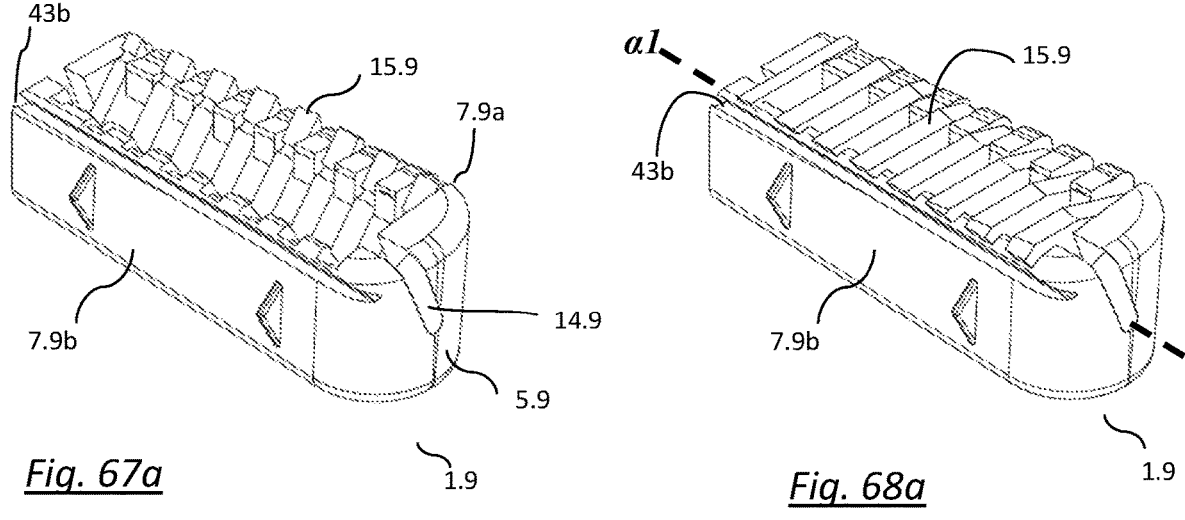
*Fig. 67a*     *Fig. 68a*
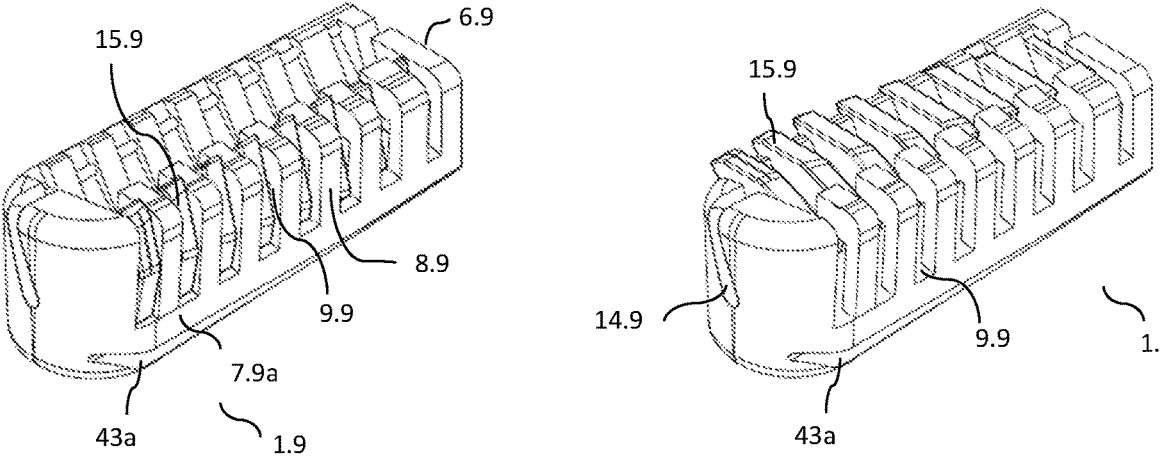
*Fig. 67b*     *Fig. 68b*

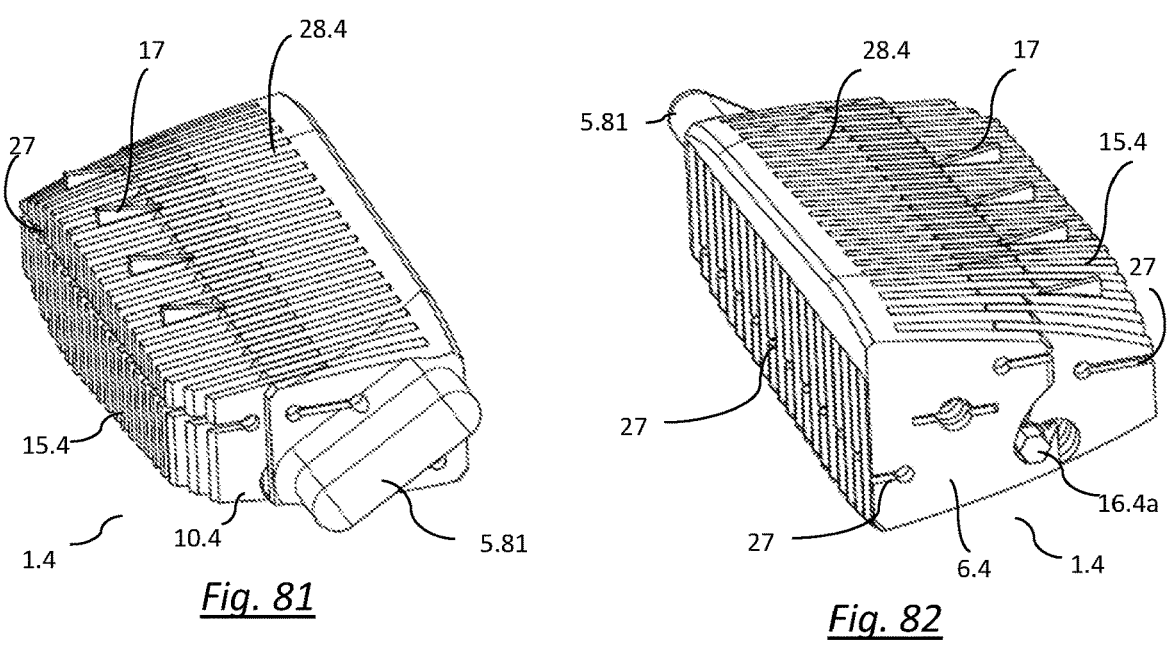
Fig. 81
Fig. 82
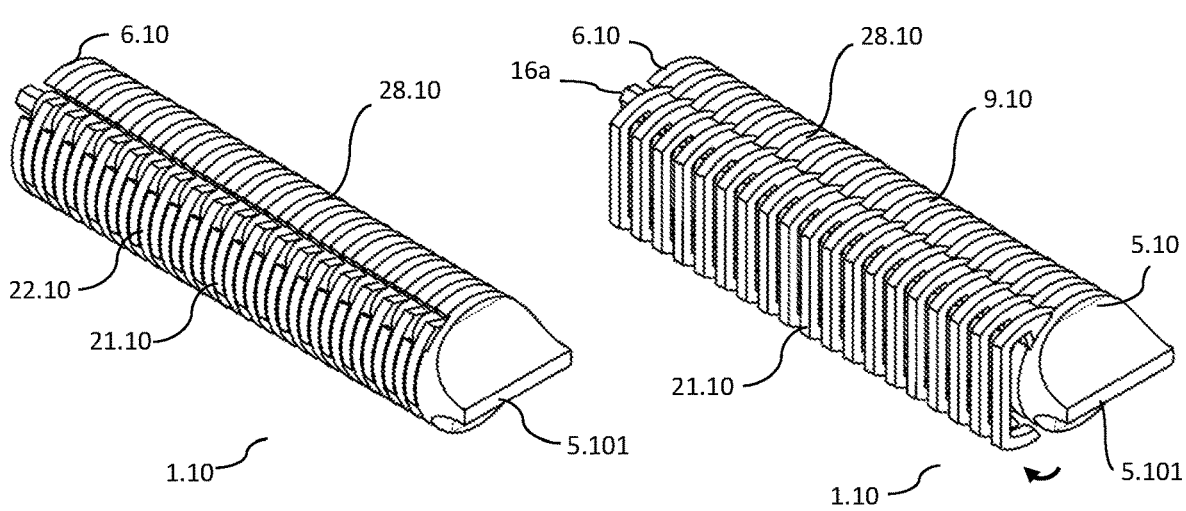
Fig. 83
Fig. 84
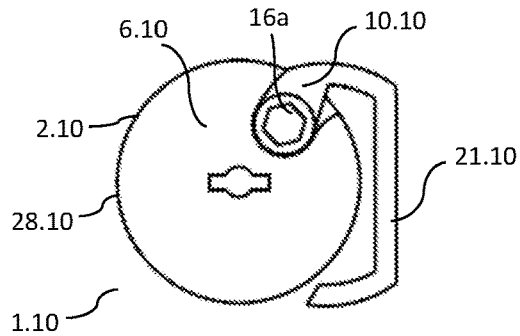
Fig. 85

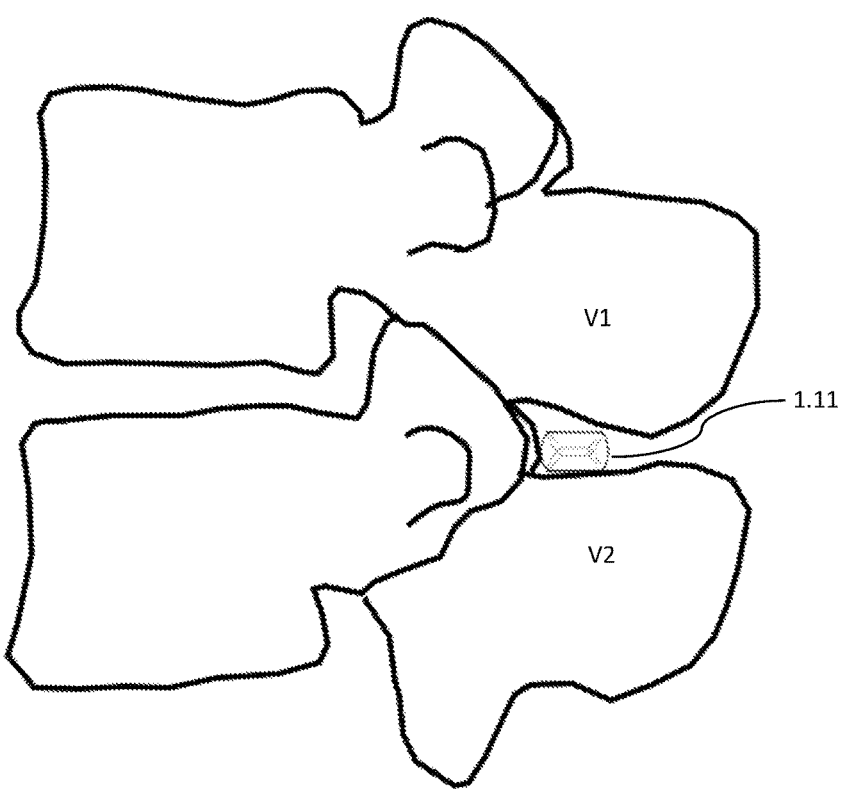
_Fig. 91_
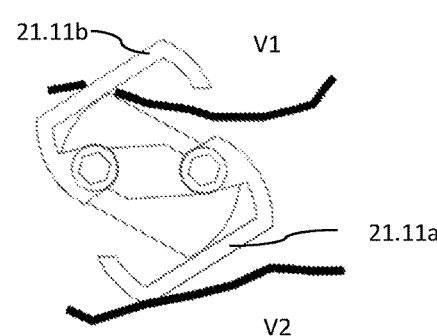
_Fig. 93_
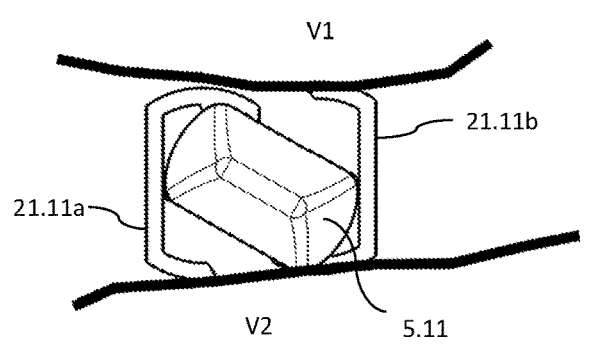
_Fig. 92_
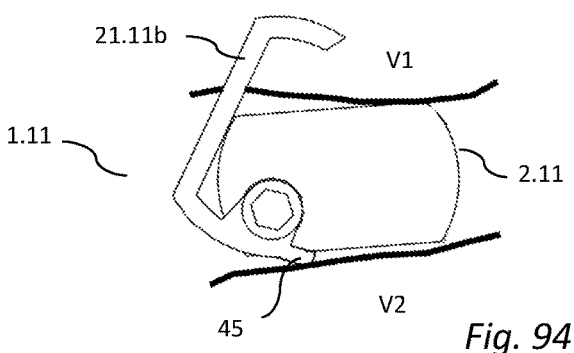
_Fig. 94_

EXPANDABLE AND MODULAR INTERVERTEBRAL IMPLANT

CROSS REFERENCE OF RELATED APPLICATION(S)

The present application is the National phase application of the international PCT Patent Application PCT/CH2021/050021 filed on Sep. 21, 2021, which claims priority from Swiss Application No.: 01211/20, filed on Sep. 23, 2020, Swiss Application No.: 00476/21, filed on May 2, 2021, Swiss Application No.: 00639/21, filed on Jun. 1, 2021, Swiss Application No.: 00716/21, filed on Jun. 18, 2021, Swiss Application No.: CH070136/2021, filed on Aug. 4, 2021 and Swiss Application No.: CH070155/2021, filed on Aug. 10, 2021, the disclosures of which are incorporated by reference herein in its entireties as part of the present application.

FIELD OF INVENTION

The present invention relates to the medical field, and more particularly to an expandable and modular intervertebral implant.

BACKGROUND

Certain pathologies of the spinal column, such as degenerated discs, facet diseases, and dislocation of vertebrae, compromise the support capacity of the column and the sharing of the load.

The treatment of such pathologies in their advanced stages is achieved by various stabilization systems with intra-discal implants such as interbody cages, which are typically coupled with extra-discal systems, which combine the use of vertebral screws and plates or rods to rigidly connect the two adjoining vertebrae. Such intra-discal implants have significantly improved the treatment of pathologies of the spinal column, by restoring the intervertebral space, which results in the decompression of the nerve roots and the acceleration of bony fusion of the adjoining vertebrae together.

Impactation cages represent an important category among interbody cages. These cages, which have a substantially parallelepiped shape, are inserted between the vertebrae by impactation. The downside of these cages is the difficulty of their insertion into the intervertebral space through narrow access routes using various surgical approaches, such as posterior, transforaminal, postero-lateral, lateral, antero-lateral and anterior approaches, in particular when interbody cages need to maximize contact surfaces with adjacent vertebrae in order to optimize the load sharing with the two adjacent vertebrae, and reproduce the natural lordosis in the lumbar spine.

In order to overcome these challenges, interbody cages which expand in situ have been developed, among which are expandable cages where the increase of the volume of the cages is achieved by a pivoting member directly engaging vertebrae and distracting the separation space between the vertebrae.

U.S. Ser. No. 13/877,851, U.S. Ser. No. 12/171,165, U.S. Ser. No. 11/276,345, U.S. Ser. No. 11/394,719, U.S. Ser. No. 09/350,984, U.S. Ser. No. 13/941,095, U.S. Ser. No. 13/605, 751, U.S. Ser. No. 13/667,551, U.S. Ser. No. 13/095,634, U.S. Ser. No. 12/993,960, U.S. Ser. No. 8,187,332, and U.S. Ser. No. 15/739,696, disclose interbody cages configured with components which pivotally engage vertebrae to dura bly expand the height of the interbody cage. Some of the references describe cages which comprise a mobile member pivoting around an axis on a longitudinal axis of another component. Among these references, U.S. Ser. No. 12/171, 165 describes a mobile member which, when pivoted within a stationary element, causes flexible members to unwind outward the stationary member, thus increasing the volume of the cage. U.S. Ser. No. 15/739,696 describes a mobile member which, when pivoted within a fixed element, directly extends outward the fixed element. The expanded volumes for the cages in these references are lopsided increases of form factors and do not manage to increase the perimeter of the contact surfaces of the cages with the adjoining vertebrae.

SUMMARY

The purpose of the present invention is to provide an interbody cage for the spinal column which increases the volume of the interbody cage from a first folded or stowed configuration to a second unfolded or deployed configuration such that the perimeters of the contact surfaces between the interbody cage and the vertebrae increase from the stowed configuration to the deployed configuration of the cage. The interbody cage of the invention is structured as a scaffold made of at least two folding and unfolding scaffoldings: one base member (also named a cage body) which receives the pivoting means of a pivoting member (also named an extension member) structured to pivot around an axis on the cage body, which axis is generally oriented towards the vertebrae at the time of insertion of the cage. The purpose of the extension member is to expand the perimeter of contact surface of the interbody cage with one vertebra or both vertebrae of a vertebral segment, or to increase the height of the interbody cage, or to increase both the perimeters of the contact surface of the interbody cage and its height. The deployment of the extension member increases the form factor of the cage to provide broader and more stable surfaces of contact with the vertebrae. In preferred embodiments, the extension member comprises blades, rings or hooks which are stowed or folded in the cage body in a first configuration and are then deployed or unfolded outwards the cage body to separate adjoining vertebrae in a second configuration, such deployment being actuated by pivoting the extension member around an axis of rotation configured within the cage body or on a surface or on a lateral side of the cage body. In other embodiments, the extension member may be configured with different shapes, such as "L" or "T" shapes or may consist in a compact block or an "open-box" quadrilateral structure.

All the embodiments of the invention may be configured with cage body structures made of thin walls and extension members configured with thin, notched and/or segmented blades, rings and/or hooks to introduce a damping feature to the implant between the two adjoining vertebrae, to mimic the natural structure of cancellous bone, prevent subsidence around the cage and are prone to enhance the bone growth around and through the interbody cage. The various embodiments of the invention may also be structured as modular scaffolds, where one same cage body may be assembled with different sizes and shapes of extension members, adjusting the assembled interbody cage to specific heights, width, lengths and other features to match the size and anatomy of the interbody space and of the vertebrae of the vertebral segment.

The Invention may also be used to separate two spinous processes and lock the processes In a distracted position.

A first method of deployment of the interbody cage is provided wherein, after the cage is positioned in its final location between the adjoining vertebrae, the vertebrae are first distracted by a rotation of the cage body ("Rotation") in order to create buffer space between the cage body and the upper and lower vertebrae for the deployment of the extension member or of two opposing extension members by pivoting said extension members, and thereafter reverse-rotating ("Reverse-Rotation") the cage body into the opposite direction to cause the upper and lower surfaces of the cage and of the extension members to rest against and anchor into the two adjoining vertebrae. In another method of deployment of a cylindric shaped cage body, the step of Rotation is not applied, and merely the extension member is deployed outwards. In yet another method, a Rotation of the cage body is first actuated for deployment of the extension members, but no Reverse-Rotation is applied, as the deployment of the extension members have locked the cage body in the rotated position after the Rotation. In yet another method of deployment of the cage, the cage body is reverse-rotated beyond the degree of the Reverse-Rotation of the first method, in order to distract the vertebral segment one second time ("Second Reverse-Rotation") to deploy another, oppositely positioned extension member, by pivoting said other opposite extension member, before rotating the cage body back again ("Second Rotation") to enable the cage body and both extension members to rest against and anchor in one or both vertebrae of the vertebral segment.

The embodiments of the Invention may apply to any constructs separating bones and/or for the fusion of any bones.

The characteristics of the invention will appear more clearly from the description of various embodiments and their variations, which are solely provided as examples and are not limitative, and in which references will notably be made to the anterior part or frontal part of the cage or body, thus defining that part of the cage which is adjusted against the vertebrae just before the introduction of said cage or body into the interbody space, and to the posterior part or rear-part of the cage body, which shall define the part of the cage opposite the anterior side or frontal part. The words "pivoted" and "rotated" are used within the same meaning, to describe a motion around an axis.

BRIEF DESCRIPTION OF DRAWINGS

The description of these various embodiments refers to the attached schematic Figures in which:

FIG. 1 represents a perspective rear view of the body of the cage of the first embodiment.

FIG. 2 represents a perspective frontal view of the body of the cage of the first embodiment.

FIG. 3 represents a perspective frontal view of a variation of the body of the first embodiment.

FIG. 4 represents a perspective frontal view of the extension member of the cage of the first embodiment.

FIG. 5 represents a perspective rear view of the cage assembly of the first embodiment in a first configuration with stowed extension member.

FIG. 6 represents the same perspective rear view of the cage assembly of FIG. 5, but in the second configuration with deployed extension member.

FIG. 18a represents a rear view of the cage of the second embodiment between two schematic vertebrae, with stowed extension members arranged as hooks.

FIG. 18b represents a rear view of the same cage as in FIG. 18a between two distracted schematic vertebrae with partially deployed hooks.

FIG. 18c represents a rear view of the same cage as in FIGS. 18a and 18b between two schematic vertebrae with fully deployed hooks.

FIG. 19 represents a perspective rear view of the cage of the third embodiment with stowed extension members.

FIG. 20 represents a perspective rear view of same cage of the third embodiment as in FIG. 19 with two sets of deployed extension members arranged as blades.

FIG. 21a represents a rear view of the same cage as in FIG. 19 with stowed blades.

FIG. 21b represents a rear view of the same cage as in FIG. 20 with deployed blades.

FIG. 22a represents a perspective frontal view of a variation of the cage of the third embodiment with deployed triangular-shaped blades.

FIG. 22b represents a different perspective frontal view of the same cage in the same configuration as in FIG. 22a.

FIG. 23 represents a top view of the same cage as in FIGS. 22a and 22b, but in the configuration of stowed extension members.

FIG. 24a represents a rear view of the same cage as in FIG. 23 and in the same configuration of stowed blades.

FIG. 24b represents a rear view of the same cage as in FIG. 24a but with deployed blades.

FIG. 25 represents a perspective frontal view of a second variation of the cage of the third embodiment with deployed thin triangular-shaped blades.

FIG. 26 represents a perspective rear view of the body of the cage of FIG. 25.

FIG. 27 represents a perspective rear view of the two extension members of the cage of FIG. 25.

FIG. 28 represents a lateral cross-section viewed from the rear of the same cage as in FIG. 25 but in the configuration of stowed blades.

FIG. 38 represents a top view of the same cage as in FIG. 37a in the same configuration of deployed blades.

FIG. 39a represents a perspective rear view of one of the two extension members of the cage of the fifth embodiment.

FIG. 39b represents a perspective rear view of the other one of the two extension members of the cage of the fifth embodiment.

FIG. 40a represents a lateral cross-section of the cage of the fifth embodiment viewed from the rear in the first configuration of stowed blades.

FIG. 40b represents the same lateral cross-section of the same cage as in FIG. 40a, but with partly deployed extension members.

FIG. 40c represents the same lateral cross-section of the same cage as in FIGS. 40a and 40b, but with fully deployed extension members.

FIG. 41 represents a perspective rear view of a first variation of the cage of the fifth embodiment in the second configuration of deployed blades.

FIG. 42 represents a rear view of the cage of FIG. 41.

FIG. 43 represents a perspective rear view of a second variation of the cage of the fifth embodiment in the second configuration of deployed blades.

FIG. 44a represents a perspective frontal view of the extension member of the cage in FIG. 43.

FIG. 44b represents a perspective rear view of the same extension member as in FIG. 44a.

FIG. 45 represents a perspective rear view of a third variation of the cage of the fifth embodiment in the first configuration of stowed hooks.

FIG. 46 represents a perspective rear view of the same cage as in FIG. 45 with partially deployed hooks.

FIG. 47 represents a perspective rear view of the same cage as in FIGS. 45 and 46 with fully deployed hooks.

FIG. 48 represents a lateral cross-section viewed from the rear of the cage of FIG. 46, in a slightly rotated position with partially deployed hooks.

FIG. 49 represents a rear view of the same cage as in FIG. 47 with fully deployed hooks.

FIG. 55a represents a frontal view of the cage of the sixth embodiment between two schematic vertebrae, with stowed sets of rings.

FIG. 55b represents a frontal view of the same cage as in FIG. 55a between two distracted schematic vertebrae with one partially deployed set of rings.

FIG. 55c represents a frontal view of the same cage as in FIGS. 55a and 55b between two schematic vertebrae with one fully deployed set of rings.

FIG. 55d represents a frontal view of the same cage as in FIGS. 55a to 55c between two distracted schematic vertebrae with one fully deployed set of rings and the other partially deploying set of rings.

FIG. 55e represents a frontal view of the same cage as in FIGS. 55a to 55d between two distracted schematic vertebrae with one fully deployed set of rings and the other partially deployed set of rings.

FIG. 55f represents a frontal view of the same cage as in FIGS. 55a to 55e between two schematic vertebrae with two fully deployed sets of rings.

FIG. 62 represents a perspective frontal view of the cage of the eighth embodiment with an oblique tip and two sets of stowed triangular blades.

FIG. 63 represents a rear view of the same cage as in FIG. 62 with one set of triangular blades fully deployed and the other set of triangular blades partially deployed.

FIG. 64 represents a perspective frontal view of the same cage as in FIGS. 62 and 63 with its two sets of triangular blades fully deployed.

FIG. 65 represents a perspective frontal view of the cage of the ninth embodiment with a delivery system.

FIG. 66a represents a frontal view of the cage of the ninth embodiment with visible distal ends of the extensions of the instrument.

FIG. 66b represents a frontal view of a smaller cage than the one represented in FIG. 66a but with the same distance between the extensions of the instrument.

FIG. 66c represents a frontal view of an even smaller cage than the one represented in FIG. 66b but still with the same distance between the extensions of the instrument.

FIG. 67a represents a perspective frontal view of the cage of the ninth embodiment with one extension member positioned along the central longitudinal axis of the body, in stowed configuration.

FIG. 67b represents another perspective frontal view of the cage represented in FIG. 67a with one extension member in stowed configuration.

FIG. 68a represents a perspective frontal view of the same cage as represented in FIGS. 67a to 67c in the second configuration with its deployed extension member.

FIG. 68b represents another perspective frontal view of the cage represented in FIG. 68a with its deployed extension member.

FIG. 81 represents a perspective frontal view of the cage represented in FIG. 80 in the second configuration with deployed extension member.

FIG. 82 represents a perspective rear view of the same cage as in FIG. 81 in the same second configuration of deployed extension member.

FIG. 83 represents a perspective frontal view of the cage of the tenth embodiment of a cage with a cylindric shaped body with stowed extension member.

FIG. 84 represents a perspective frontal view of the same cage as in FIG. 83 but with a deployed extension member arranged with a set of flat-sided parallel hooks.

FIG. 85 represents a rear view of the same cage as in FIG. 84 in the same configuration with deployed extension member.

FIG. 91 represents a view of a vertebral segment with the inserted interspinous implant of the eleventh embodiment of the invention in stowed configuration.

FIG. 92 represents a close-up of the same view as in FIG. 91 with the same interspinous implant but in a second configuration with deployed extension members.

FIG. 93 represents a variation of the implant of the eleventh embodiment with one hook-shaped deployed extension member to distract the space between two vertebrae and another hook shaped extension member to prevent the migration of the implant.

FIG. 94 represents another variation of the implant of the eleventh embodiment with one single deployed extension member both distracting the space between two vertebrae and preventing the migration of the implant.

DETAILED DESCRIPTION

Figures 7, 8, 9, 10, 11, 12A, 12B:
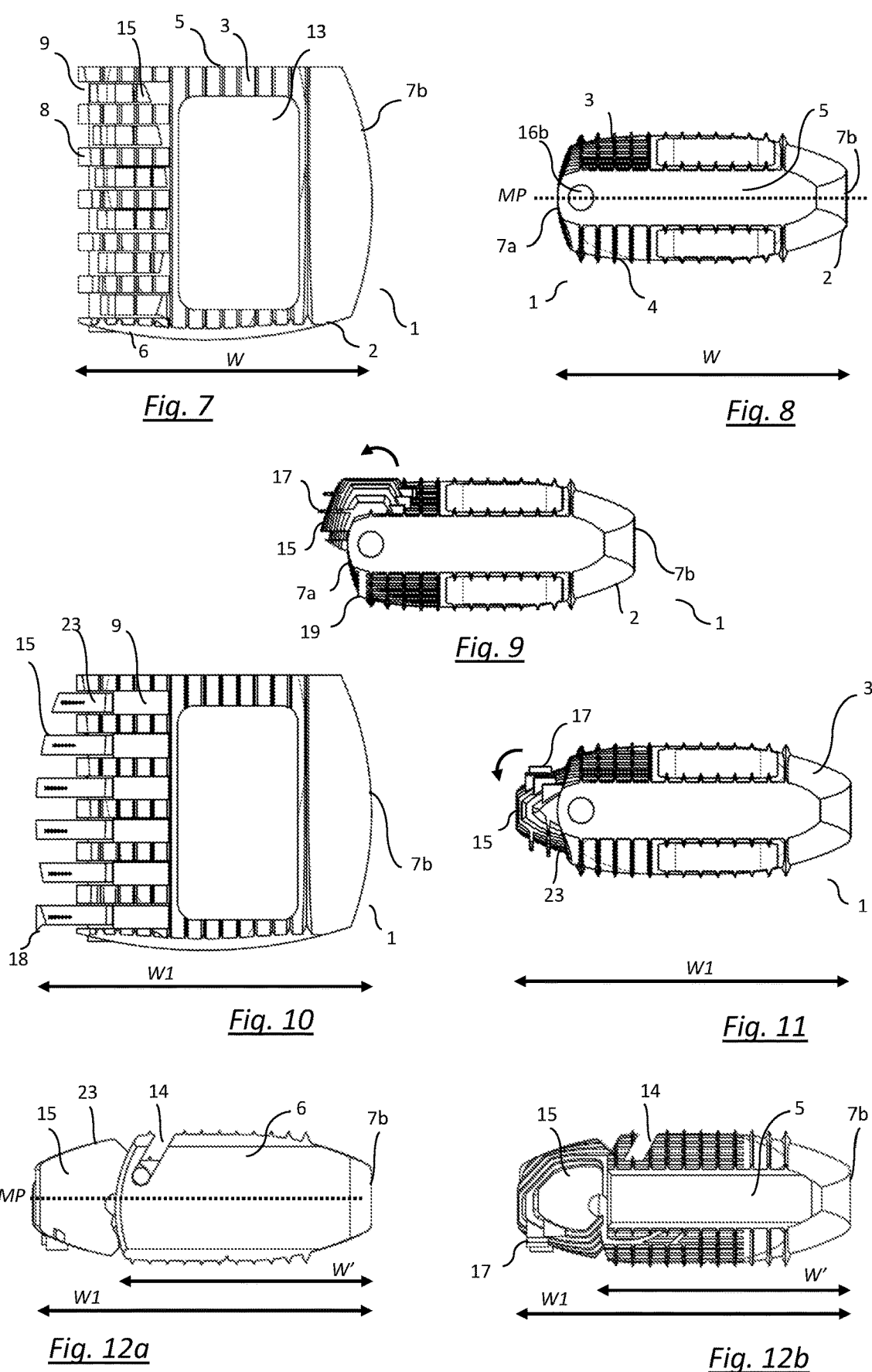
FIG. 7 represents a top view of the cage assembly represented in FIG. 5 with stowed extension member.
FIG. 8 represents a frontal view of the same cage as in FIGS. 5 and 7 in the same first configuration of stowed extension member.
FIG. 9 represents a frontal view of the same cage as in FIGS. 5, 7 and 8 with partially deployed extension member.
FIG. 10 represents a top view of the cage assembly represented in FIG. 6 in a second configuration with fully deployed extension member.
FIG. 11 represents a frontal view of the same cage as in FIG. 10 in the same second configuration with fully deployed extension member.
FIG. 12a represents a rear view of a variation of the cage of the first embodiment with an ex-centered pivoting axis in the second configuration of a fully deployed extension member.
FIG. 12b represents a frontal view of the same cage as in FIG. 12a in the same second configuration.

According to FIGS. 1 to 6, the first embodiment of the invention describes an interbody cage 1, for an anterior surgical approach, with a body 2 having an essentially planar upper surface 3 configured to rest against a upper vertebra V1, an essentially planar lower surface 4 configured to rest against a lower vertebra V2, an anterior part 5, which is the part which first accesses the intervertebral space between two vertebrae V1, V2, a rear part 6 which is opposite the anterior part 5, and two lateral sides 7*a*, 7*b*. According to FIGS. 1 and 2, the dimensions of the body 2 between the anterior 5 and rear 6 parts (which will be defined as "length") and between the lateral sides 7*a*, 7*b* (which will be defined as "Width W" or "W") are relatively similar. The upper surface 3 and lower surface 4, which have a slight convex shape, are separated by a distance defining the height of the body 2 (which may also be defined as "Thickness" of the body 2 or the cage 1). The dimension of the Thickness of the body 2 is substantially smaller than the dimensions in length and in width 'W' of the body 2, such Thickness being angled in the length of the body 2, with a Thicker rear part 6 and a slimmer anterior part 5. The Thickness defines an overall cushion shape of the body 2 in both length and width "W" which may be appropriate to match the anatomy of concave vertebral plates. In different variations of this first embodiment, the body 2 may be angled between the lateral sides 7*a*, 7*b* instead of in its length, or be configured with essentially parallel upper surface 3 and lower surface 4. The upper surface 3 and lower surface 4 of the body 2 may be smooth or covered partly or entirely with crenellations to prevent the cage 1 from migrating within the interbody space or from being expelled outside of the interbody space. One lateral side 7*b* of the body 2 has a curved surface between the anterior part 5 and the rear part 6, while the other lateral side 7*a* has a jagged shape, made of alternating walls 8 and slits 9. This lateral side 7*a* is configured to receive an extension member 10. Round openings 11 are arranged in the walls 8, in the anterior part 5 and in the rear part 6 to receive the base 12 of the extension member 10 along an axis "α". The body 2 has a cavity 13 which may contain bone graft. FIG. 3 represents a variation of the body 2 of the cage 1 of the first embodiment, wherein the openings 11 arranged in the walls 8 of the lateral side 7*a* and in the anterior part 5 and rear part 6 of the body 2 are replaced by channels 14 configured to receive the base 12 of the extension member 10 and to allow its pivoting around the axis "α" at the bottom of said channel 14.

According to FIG. 4, the extension member 10, has a longitudinal structure with a base 12 which is shaped as a rod with a proximal end 16*a* and a distal end 16*b*, on which parallel blades 15 are mounted. The proximal end 16*a* of the base 12 may have an imprint (as shown in FIGS. 30, 35, 48, 49 and 78) or a hexagonal cross-section (as shown in FIGS. 22*a* to 24*b*, 59, 62 and 82) to receive or otherwise engage the tip of the rod of a delivery instrument. The base 12 is configured to be received in openings 11 or at the bottom of channels 14 arranged in the walls 8 of the body 2. The blades 15 have a thickness which is marginally smaller than the width of the slits 9 arranged in the lateral side 7*a* of the body 2, which slits 9 are suited to receive the blades 15 of the extension member 10 in one of the configurations of the cage assembly 1. The upper and lower bone-engaging tranches 23 of the blades 15 are angled relative to each other, with blades 15 having a higher dimension closer to the base 12, giving the blades 15 an overall trapezoidal contour. In variations of the invention, the blades 15 may have any other shapes of contours: square, rectangular (as in FIG. 21*b*), triangular (as in FIGS. 24*b* and 64), longitudinal (as in FIGS. 39*a* and 40*c*), semi-hooked (as in FIGS. 40*b* and 40*c*) or oblong, circular, oval etc.

As shown in FIG. 5, in the first configuration of the cage assembly 1 comprising the body 2 and the extension member 10, the blades 15 of the extension member 10 are stowed within the slits 9 in the body 2. The round openings 11 in the walls 8 of the body 2 have received the base 12 of the extension member 10, and its proximal and distal ends 16*a*, 16*b* are approximately level with the surfaces of the anterior part 5 and rear part 6, respectively, of the body 2. The distance between the upper and lower bone-engaging tranches 23 of the blades 15 is preferably smaller than the dimension of the Thickness of the body 2 when the extension member 10 is stowed in the body 2 in this first configuration. The slits 9 in the lateral side 7*a* of the body 2 are deep enough to receive the full width of the blades 15 when said blades 15 are fully stowed. According to FIGS. 5, 7 and 8, no portion of the blades 15 or other parts of the extension member 10 protrude from the lateral side 7*a* of the body 2, but in variations of this embodiment, some portions of the extension member 10 may protrude from the lateral side 7*a* and/or upper surface 3 or lower surface 4 of the body 2 in this first configuration of stowed blades 15.

According to FIGS. 6, 10 and 11, the extension member 10 may be deployed outward laterally beyond the lateral side 7*a* from the body 2, from the first configuration into a second configuration, by a rotation of approximately 180° of the base 12 around its axis "α" of rotation.

FIG. 9 describes an extension member 10 partially deployed from the body 2 (after approximately a 90° rotation of the base 12) and FIGS. 6, 10, 11, 12*a* and 12*b* describe a fully deployed extension member 10. In this second configuration of the cage assembly 1, the width W of the body 2 is now extended to the width W1 of the full cage assembly 1. In the second configuration of the cage assembly 1, the height of the blades 15 of the extension member 10 is similar to the Thickness of the body 2 at its cross-section symmetrically opposite towards the other lateral side 7*b* of the body 2, so as to preferably give a symmetrical shape to the cage assembly 1 in the deployed configuration. In this deployed configuration, the upper surface 3 and the lower surface 4 of the body 2 and the two bone engaging tranches 23 defining the height of the blades 15 of the extension member 10 may all rest against the upper and lower vertebrae V1, V2.

Figures 13, 14, 15, 16, 17:
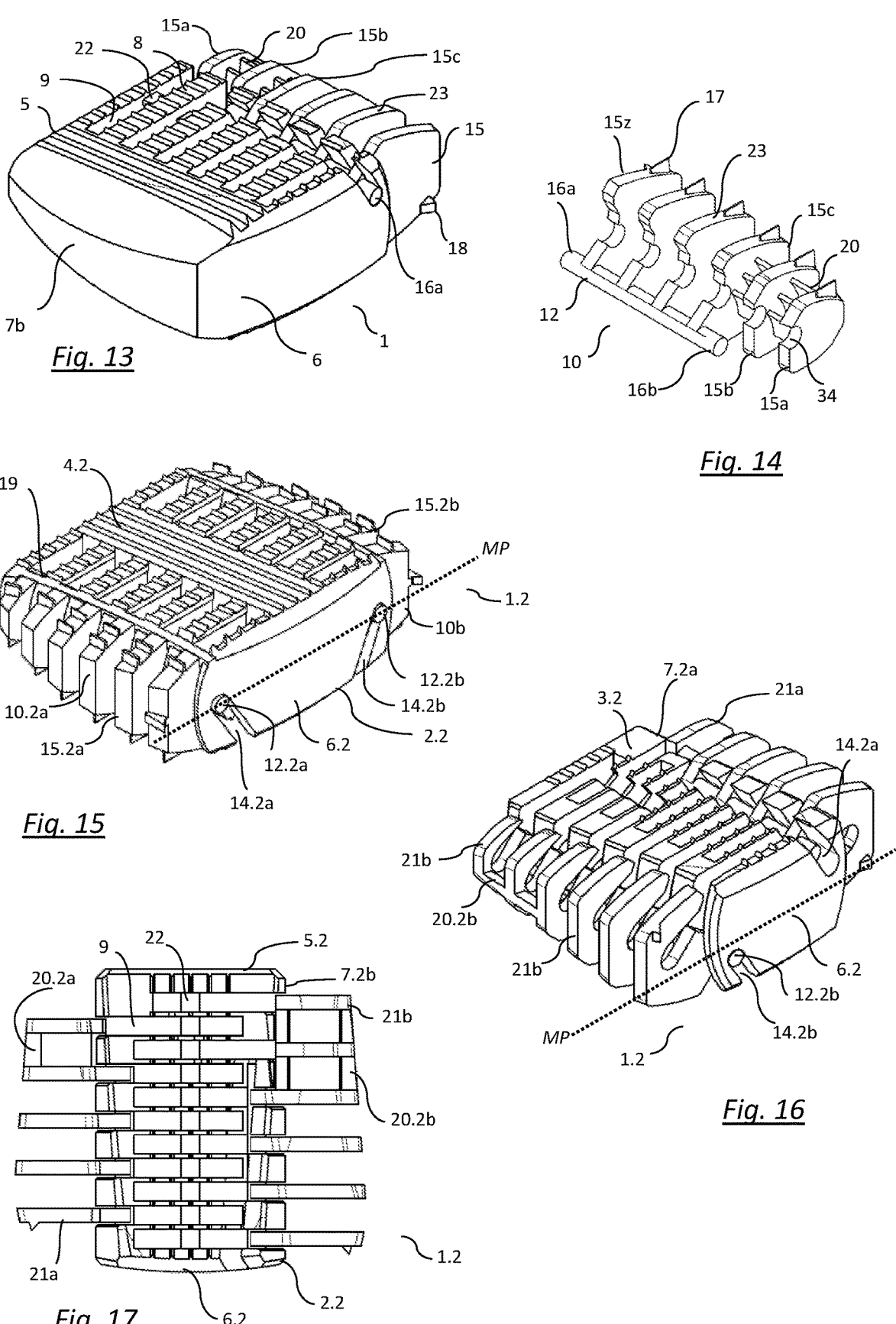
FIG. 13 represents a rear perspective view of the cage with ex-centered axis of rotation of the extension member in the deployed configuration.
FIG. 14 represents a frontal perspective view of the extension member of the cage in FIG. 13.
FIG. 15 represents a rear perspective view of the cage of the second embodiment represented upside-down with two deployed extension members.
FIG. 16 represents a rear perspective view of a variation of the cage of the second embodiment with two ex-centered pivoting axes and deployed extension members.
FIG. 17 represents a top view of the cage of FIG. 16 with two deployed extension members.
Figure 29:
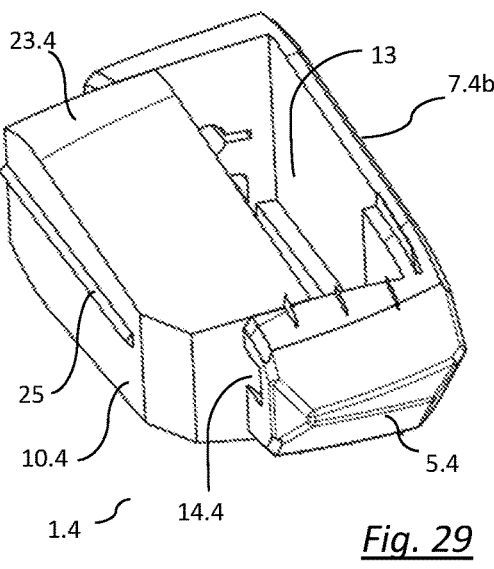
FIG. 29 represents a perspective frontal view of the cage of the fourth embodiment for an oblique approach with a deployed block-shaped extension member.

The advantage of this invention is that the access route for the cage 1 into the intervertebral space may be narrower, so that the width of the aperture cut into the anterior ligament can be smaller and preserve some of the stabilization properties of that ligament. The same is true for the annulus of the disc, which only requires a reduced aperture according to the invention, thus preserving a larger biologic ring around the interbody space. In addition, the extension member 10 is deployed behind the annulus and the preserved part of the anterior ligament, both of which constitute an additional barrier preventing the expulsion of the cage 1. FIGS. 6, 9 and 11 also describe thin anchors 17 placed on the bone-engaging tranches 23 of the blades 15 to help further anchor the blades 15 and the cage 1 into the vertebral plates of the vertebrae V1, V2. FIGS. 6, 10 and 13 also describe a lateral hook 18 configured near the lateral tranche of the last blade 15, which may anchor laterally into the inner wall of the annulus during the deployment of the extension member 10 and may thus further prevent the migration of the cage 1.

The extension member 10 may be prevented from deploying beyond a 180° rotation around its axis 12 by any constraining means arranged on the body 2, such as the constraining bar 19 shown in FIGS. 5, 9 and 15, connecting the walls 8 of the body 2 on its lower surface 4. As shown in FIG. 8, the deployment of the blades 15 of the extension member may also be constrained beyond a 180° rotation by the lower surface 4 of the body 2 reaching until the lateral side 7*a* of the body 2. Other means of constraints can be configured on the lower surface 4 of the body 2 to constrain the deployment of the extension member. In different variations of the invention, the extension member 10 may be configured to rotate around its axis beyond a 180° rotation of its base 12, which may be advantageous to give the cage 1 flexibility in matching the vertebral plates' anatomy: while the upper and lower surfaces 3 and 4 of the body 2 present rigid planes resting against the vertebrae V1, V2, the joints between said lower surfaces 3 and 4 of the body 2 and the surfaces defined by the bone-engaging tranches 23 of the blades 15 of the extension member 10 may be angled at different planes than those of the surfaces 3, 4 of the body 2, and better match the anatomy of the vertebrae V1, V2. To enhance the flexibility of the cage 1 to adjust to such anatomy, the body 2 may be configured with openings 11 having a larger diameter than the diameter of the base 12 of the extension member 10, to give the extension member 10 wiggle room for mobility within the opening 11. The same can be achieved with channels 14 configured in the body 2 with a larger bottom than the diameter of the base 12. The coupling of the flexibility of an unconstrained extension member 10 and of the mobility offered by the wiggle-room, results in full three dimensional mobility of the extension member 10 relative to the body 2.

The insertion of the cage 1 between two vertebrae V1, V2 is achieved by impaction. Once the cage 1 has reached its desired position between two vertebrae V1, V2, the deployment of the extension member 10 may be facilitated by applying the deployment method described in FIGS. 18*a* to 18*c*, wherein the body 2 is first slightly rotated between vertebrae V1, V2 so as to distract said vertebrae and thus create sufficient buffer space above portions of the upper surface 3 and lower surface 4 of the body 2 to deploy the extension member 10 without forcing blades 15 against the vertebra V1 or V2 in their rotational radius. The deployment of the extension member 10 outwards of the body 2, to increase the cage Ts form factor from the first configuration of the cage 1 to the second configuration with the full extension of the extension member 10, may be actuated with any appropriate instrument configured to engage the proximal end 16*a* of the base 12 of the extension member 10.

FIGS. 12*a*, 12*b* and 13 represent a variation of the invention of the cage 1 of the first embodiment, wherein channels 14 in lieu of round openings 11 are arranged in the anterior part 5 and rear part 6 of the body 2 and in the walls 8 of the body 2. The advantage of this variation of the cage assembly 1 is that the extension member 10 may be slotted into the body 2 of the cage 1 represented in FIG. 3 just prior to the insertion of the cage 1 between the vertebrae V1, V2, thus allowing the surgeon to choose a preferred feature, shape or dimension of the extension member 10 best fitting the individual spinal anatomy. In as much, the cage 1 of this variation is modular, with a variety of optional extension members 10 configured to fit one individual body 2, thus composing a variety of different optional cage assemblies 1.

In addition, according to FIGS. 12*a*, 12*b*, 13 and 16, the bottom of the channels 14 are arranged in the anterior part 5 and rear part 6 of the body 2 and in the walls 8 of the body 2 in an ex-centered configuration: this enables the body 2 to receive the base 12 of the extension member 10 in an ex-centered axis relative to the median horizontal plane "MR" cutting through the central axis "a" In this variation, additional stowage space is created for the blades 15 within the slits 9 between the walls 8 of the body 2: the Thickness of the body 2 may thus be used in addition to the depth of the slits 9 in the body 2 to host wider blades 15 of the extension member 10. According to FIGS. 12*a* and 12*b*, the cage 1 with ex-centered base 12 with fully deployed blades 15 has the same width W1 as the width W1 of the cage 1 having a base 12 configured on the median horizontal plane "MP" with deployed blades 15 represented in FIG. 11, yet the width W of the body 2 with ex-centered bottom of channel 14 is substantially smaller than the width W of the body 2 of the cage 1 shown in FIGS. 7 to 11, which has the round openings 11 positioned on the median horizontal plane "MP" cutting through axis "α". The closer the round openings 11 or bottom of channels 14 are positioned to the upper surface 3 or lower surface 4 of the body 2, the wider the blades 15 of the extension member 10 can be configured.

FIG. 14 represents an extension member 10 for a cage 1 whose body 2 has a high angulation between its anterior part 5 and its rear part 6 and is configured with ex-centered bottoms of channels 14. A base 12 of the extension member 10 configured in an ex-centered channel 14 may not fit across the whole length of such a high angled body 2 and would protrude from the upper surface 3 or from the lower surface 4 of the body 2 before reaching the anterior part 5 of the body 2 because of its substantially smaller Thickness than at the level of its rear part 6. According to FIG. 14, the length of the base 12 between its proximal end 16*a* and its distal end 16*b* is shorter than the distance from the first blade 15*a* to the last blade 15*z*, and the first two blades 15*a* and 15*b* are not attached to the base 12: instead, the first blade 15*a* is attached to the second blade 15*b* via curved connectors 20, and the second blade 15*b* is attached to the third blade 15*c* also via curved connectors 20; the third blade 15*c* is directly attached to the base 12 close to its distal end 16*b*. The rotation of the first two blades 15*a*, 15*b* is actuated by the rotation of the base 12 via the third blade 15*c*. The curved structure of the curved connectors 20 are received by curved slits in the upper surface 3 and lower surface 4 of the body 2: this saves material in the body 2 compared to straight connectors which would have a cammed rotational trajectory. An alternative for the configuration of extension members 10 for high angled cages 1, consists in arranging the bottoms of the channels 14 in an oblique axis relative to the central longitudinal axis "α" of the body 2. As shown in FIG. 14, the blades 15 are configured with a circular opening 34 to circumvent the thickness of the longitudinal structure 22 connecting the walls 8 of the body 2.

Figure 78:
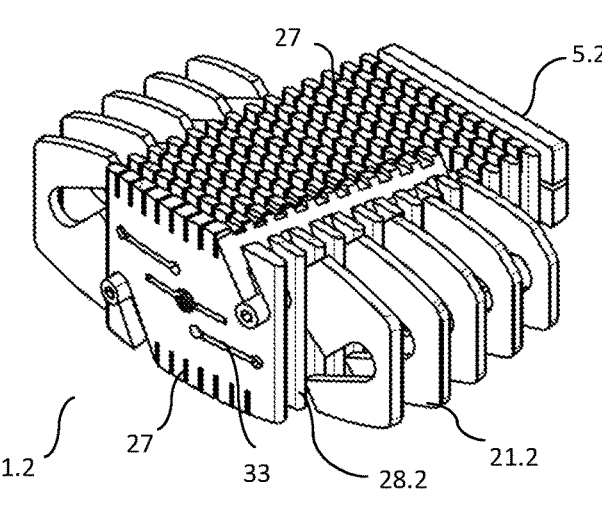
FIG. 78 represents a perspective rear view of a variation of the cage of the second embodiment with thin walls and deployed thin hooks.
Figure 79:
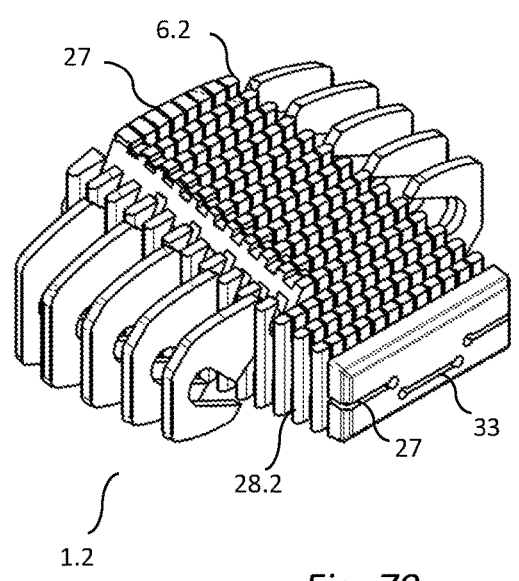
FIG. 79 represents perspective frontal view of the same cage as in FIG. 78.

In the second embodiment of the invention shown in FIGS. 15 to 18*c* and in FIGS. 78 and 79, the cage 1.2 is configured with a body 2.2 which receives two extension members 10.2*a* and 10.2*b* arranged to be outwardly deployed according to the invention beyond each of the lateral side 7.2*a*, 7.2*b* of the body 2.2. Due to the doubling factor of the width of the hooks 21 *a*, 21 *b* of the extension members 10.2*a*, 10.2*b*, the width W of the body 2.2 of the cage 1.2 of this second embodiment may be substantially narrower than the width W of the body 2 of the cage 1 of the first embodiment, while the fully deployed cage assembly 1.2 achieves the same width W1 as the width W1 of the cage 1 of the first embodiment. FIG. 15 represents a cage 1.2 with two extension members 10.2*a*, 10.2*b* arranged to have their base 12.2*a*, 12.2*b* received in the bottom of two channels 14.2*a*, 14.2*b* configured on the median horizontal plane "MP" of the body 2.2. Both channels 14.2*a*, 14.2*b* have their access on the upper surface 3.2 of the body 2.2. Constraining bars 19 are arranged on the lower surface 4.2 of the body 2.2 to prevent a rotation of the two extension members 10.2a, 10.2b beyond 180°.

FIGS. 16 and 17 represent a variation of the cage 1.2 of the second embodiment of the invention, with the bottom of the two channels 14.2a, 14.2b configured ex-centrically from the median horizontal plane "MP of the body 2.2 in order to receive two extension members 10.2a, 10.2b with wider hooks 21a, 21b: this duplicates the benefit described in FIGS. 12a and 12b for the ex-centered single extension member 10 of the cage 1 of the first embodiment. Contrary to the cage 1.2 of the second embodiment shown in FIG. 15, the two extension members 10.2a, 10.2b of this variation are slotted in their respective channels 14.2a, 14.2b each from an opposing surface 3.2, 4.2 of the body 2.2. A longitudinal connecting structure 22 connecting the walls 8.2 from the anterior part 5.2 to the rear part 6.2 of the body 2.2, increases the stability of the structure of the body 2.2, which can be advantageous to preserve said structure of the body 2.2 when it is rotated during the deployment of the extension members 10.2a, 10.2b, as shown in FIG. 18b. According to FIG. 16, the extension members 10.2a, 10.2b are configured with hooks 21a, 21b connected to the base 12.2a, 12.2b of the extension members 10.2a, 10.2b, instead of blades 15. The first hook 21a is not directly connected to the extension member 10.2a, but via the second hook 21a by one straight connector 20.2a while the first two hooks 21b are not directly connected to the base 12 of the extension member 10.2b either, but to the third hook 21b via straight connectors 20.2b. The hooks 21a, 21b circumvent the longitudinal connecting structure 22 when they are fully stowed within the body 2.2 in the first configuration of the cage 1.2. During their pivotal deployment, the hooks 21a, 21b circle around the longitudinal connecting structure 22. The hooks 21a, 21b may also increase the anchoring properties of the extension members 10.2a, 10.2b into the vertebrae V1, V2.

FIGS. 18a to 18c represent the method of deployment of the extension members 10.2a, 10.2b of the variation of the cage 1.2 of the second embodiment of the invention. After its introduction in the intervertebral space, and after it reaches its final position between the vertebrae V1, V2, the cage 1.2 is positioned with its upper surface 3.2 and lower surface 4.2 level with the vertebrae V1, V2, as shown in FIG. 18a. FIG. 18b then describes the cage 1.2 while the body 2.2 is rotated laterally. This may be actuated with any adequate instrument, engaging the rear part 6.2 of the body 2.2 and actuating a lateral rotation between 15°-25° as shown in FIG. 18b. The rotation of the body 2.2 slightly distracts the vertebrae V1, V2, and induces buffer spaces on lateral portions of the upper surface 3.2 and lower surface 4, respectively, of the body 2.2, from which the hooks 21a, 21b may be deployed by the individual lateral pivoting by approximately 180° of the two extension members 10.2a, 10.2b. Such individual rotations may be actuated simultaneously or sequentially by any instrument engaging with the respective proximal ends 16.2a of each of the bases 12.2a, 12.2b of the extension members 10.2a, 10.2b. As shown in FIG. 18c, once the hooks 21a, 21 b are fully deployed, a reverse rotation of between 15°-25° is actuated on the body 2.2. of the cage 1.2 through the instrument, which establishes durable resting of the vertebrae V1, V2 on the upper surface 3 and lower surface 4 of the body 2.2 and on the bone-engaging tranches 23 of the hooks 21a, 21b.

A third embodiment of the invention is described in FIGS. 19 to 21b, of a cage 1.3 configured to be inserted between two vertebrae V1, V2 via a lateral approach and to restore the natural lordosis of the vertebrae by a lateral angulation.

As shown in FIGS. 21a and 21b, the body 2.3 of the cage has a trapezoidal cross-section, with one lateral side 7.3a shorter than the other lateral side 7.3b. Shielding rails 24 are arranged on the upper surface 3.3 and lower surface 4.3 of the body 2.3 to shield the vertebrae V1, V2 from the rougher upper surface 3.3 and/or lower surface 4.3 of the body 2.3 when the cage 1.3 is introduced between the vertebrae in its first configuration with stowed extension members 10.3a, 10.3b; the shielding also facilitates the controlled insertion of the body 2.3 between the vertebrae V1, V2. Shielding rails 24 arranged in the direction shown in FIGS. 19 and 20 also prevent the cage 1.3 from migrating laterally towards the anterior side of the vertebrae or towards the spinal canal.

In the first configuration of the cage assembly 1.3 represented in FIGS. 19 and 21a, when the blades 15.3a, 15.3b are stowed in the body 2.3, that body has a reduced profile both in Thickness and in Width W, which is favorable for a narrow access route to the spine and facilitates the insertion of the body 2.3 between the vertebrae V1, V2. According to FIG. 21b, once the two extension members 10.3a, 10.3b are deployed applying the method described in FIGS. 18a to 18c, the from factor of the cage 1.3 is increased and the cage is extended in its width W1 by the width of the blades 15.3b resting against both vertebrae V1, V2. The form factor of the cage 1.3 is also increased in its height (Thickness) by the deployment of the triangular-shaped blades 15.3a beyond the lower surface 4.3 of the body 2.3, said blades 15.3a only resting against the lower vertebra V2 with their respective bone-engaging tranche 23. Due to the extended dimension of the bone-engaging tranches 23 of the blades 15.3a, the form factor of the cage 1.3 is also increased on the lateral side 7.3a of the cage 1.3 extending the contact surface of the cage 1.3 on the lower vertebrae V2 to a width W1 which is greater than W1 of the contact surface of the upper surface 3.3 of the cage 1.3 and blades 15.3b with the upper vertebra V1. As shown in FIG. 21b, the bone-engaging tranches 23 of the blades 15.3a are configured perpendicularly to the shielding rails 24 so that the cage 1.3 is protected against a migration in all directions. According to FIGS. 20 and 21b, the bone-engaging tranches 23 of the blades 15.3a may also have beveled profiles, which increase the anchoring properties of the blades 15.3a, 15.3b into the vertebrae V1, V2 and further prevent a migration of the cage 1.3 towards one of the lateral sides of the vertebrae. According to FIGS. 20, 22a and 22b, a pivoting shielding rail 25 is mounted on the blades 15.3a on the surfaces of one of their side-tranches connecting all blades 15.3a. The benefits of such a pivoting shielding rail 25 is to shield the vertebrae in the same way as the shielding rails 24 achieve during the insertion of the cage 1.3 between the vertebrae V1, V2, and also to strengthen the structure of the blades 15.3a on the extension member 10.3a. The additional merits of the invention are that the pivoting shielding rails 25 may be configured on stowed extension members 10.3 in a way that they do not hamper such stowage, yet they protrude from the upper surface 3.3 or lower surface 4.3 of the body 2.3 to serve their shielding purpose; in the second configuration of the deployed extension member 10.3, the pivoting shielding rail 25 lose that shielding purpose, but continue to serve the purpose of strengthening the structure of the extension member 10.3.

FIGS. 22a to 24b describe a first variation of the third embodiment of a cage 1.3 comprising a body 2.3 which, as shown in FIG. 24a, has a smaller Thickness than the Thickness of the body 2.3 of the cage 1.3 of the third embodiment shown in FIG. 21a on their respective laterals sides 7.3a. This is beneficial as it further reduces the dimension of the required access route for the cage 1.3 progressing towards the vertebrae V1, V2. Given the reduced space for stowing the blades of the second extension member 10.3*b*, such second extension member 10.3*b* has been configured with triangular-shaped blades 15.3*b* as well. FIG. 28 (representing another variation of the third embodiment), shows the limited space between the two bases 12.3*a*, 12.3*b*, with little buffer space within the body 2.3 for the triangular shaped blades 15.3*a*, 15.3*b* to revolve around their axes without being stopped by the other respective base 12.3*a* or 12.3*b*. At the base of each of the triangular-shaped blades 15.3*a*, 15.3*b*, longitudinal buttresses 26*a*, 26*b* have been configured: according to FIG. 24*b*, buttresses 26*a* extend the contact surface of the cage 1.3 with the upper vertebra V1 and buttresses 26*b* extend the contact surface of the cage 1.3 with the lower vertebra V2. FIGS. 22*a* and 22*b* also describe that both sets of blades 15.3*a*, 15.3*b* are configured with a pivoting shielding rail 25 to second the function of the shielding rails 24 for the insertion of the cage 1.3, as shown in FIG. 23. FIGS. 22*a* and 24*b* also show notches 27 arranged on the bone-engaging tranches 23 of the blades 15.3*a*, 15.3*b*, to enhance the anchoring features of the beveled bone-engaging tranches 23.

FIGS. 25 to 28 represent a second variation of the third embodiment, where the cage 1.3 has a body 2.3 configured with thin walls 28 between which the thin triangular blades 15.3*a*, 15.3*b* arranged on the extension members 10.3*a*, 10.3*b* may be stowed and deployed. The advantage of this variation of the third embodiment is to offer a denser and more homogenous surface of contact for the vertebrae by the blades 15.3*a*, 15.3*b* and upper surface 3.3 and lower surface 4.3 of the body 2.3. The structure of the body 2.3 of this variation is also strengthened by the mounting of an internal longitudinal connecting structure 22 between the anterior part 5.3 and the rear part 6.3 of the body 2.3. The connecting structure 22 has a curved cross-section which may allow blades 15.3*a* arranged with a curved slit 29 to deploy the full width of their bone-engaging tranches 23 without being hampered by the obstacle of the longitudinal connecting structure 22. As also shown in FIG. 27, the base 12.3 of the extension member 10.3 may have different dimensions across its length: the diameter of the proximal end 16.3*a* and of the distal end 16.3*b* of the base 12.2 is smaller than the diameter therebetween. This non-continuous dimension may be useful to optimize the fitting of the base 12.3 within smaller or larger channels 14.3 within the body 2.3.

Figure 30:
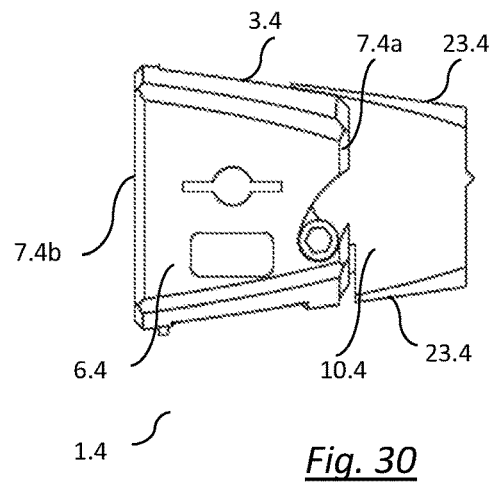
FIG. 30 represents a rear view of the cage of FIG. 29 with its deployed extension member.
Figure 31A:
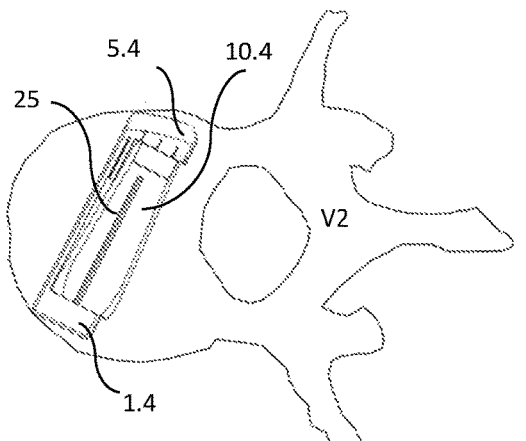
FIG. 31a represents a top view of the cage of the fourth embodiment positioned on one vertebral body, with stowed extension member.
Figure 31B:
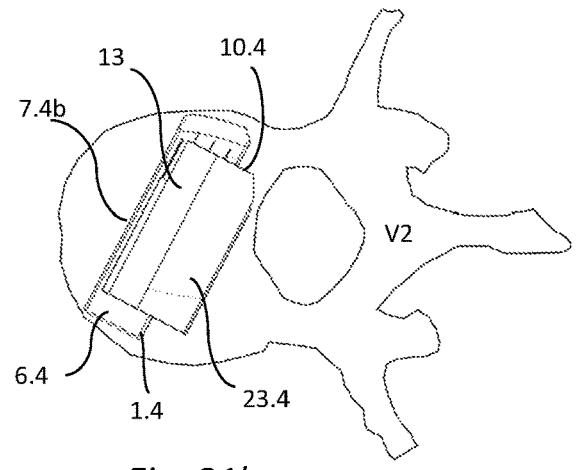
FIG. 31b represents the same top view of the cage and vertebral body as in FIG. 31a, but with deployed block-shaped extension member.

In a fourth embodiment of the invention shown in FIGS. 29 to 31*b*, the cage 1.4 may be used for an oblique approach to the vertebrae V1, V2. The height of the anterior part 5.4 of the body 2.4, which will be positioned closer to the spinal canal, is shorter than the height of the rear part 6.4, which is consistent with the natural lordosis of the lumbar spine. The extension member 10.4 is configured as a single block structure in an essentially trapezoidal shape, which is stowed in a receiving cavity 13 of the body 2.4 of the cage 1.4 and deployed by pivoting around the axis of its base 12.4 within the channel 14.4 arranged in the lateral side 7.4*a* of the body 2.4. The block-shaped structure may be beneficial for an extension member 10.4 which is made of bone-growth promoting material, such as bone-blocks, porous alloys, or compacted strands of metal or synthetic materials. In variations of this fourth embodiment, the shape of the extension member 10.4 may also be arranged as an open box with five sides or a hollow-walled structure with four walls only, in which bone-graft or other biomaterial or synthetic material may be packed, or as a different geometrical shape, such as rectangular, round, oval or triangular. The pivoting shielding rail 25 arranged on the block of the extension member 10.4 when such extension member is stowed within the cavity 13 of the body 2.4 is designed to shield-off the vertebrae from abrasive surfaces on the block of the extension member 10.4. After the deployment of the extension member 10.4, as shown in FIGS. 30 and 31*b*, the surface with the pivoting shielding rail 25 moves to a lateral position on the cage 1.4, and the two bone-engaging surfaces 23.4 of the extension member 10.4 may anchor in the vertebrae V1, V2.

Figure 32:
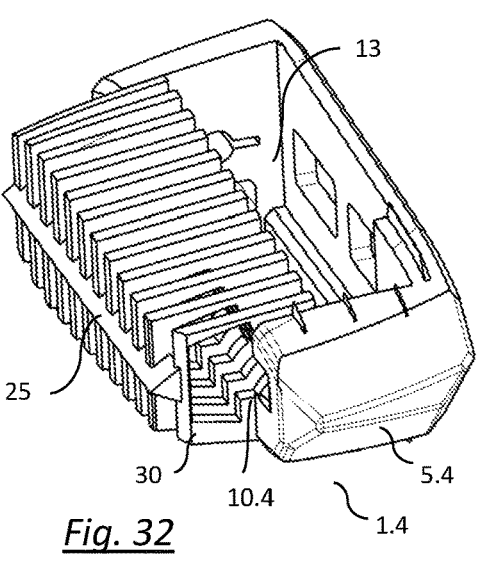
FIG. 32 represents a perspective frontal view of a first variation of the cage of the fourth embodiment for an oblique approach with a deployed extension member composed of parallel rings.
Figure 33:
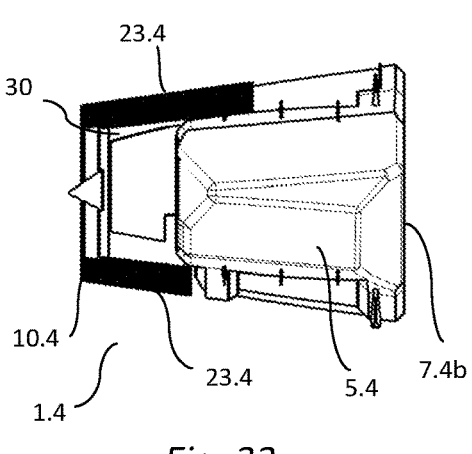
FIG. 33 represents a frontal view of the cage of FIG. 32 with its deployed extension member.

FIGS. 32 and 33 represent a first variation of the fourth embodiment, where the extension member 10.4 is configured in a succession of parallel rings 30 attached to the base 12.4 and connected by a pivoting shielding rail 25. The contours of the rings 30 essentially reflect the contours of the block of the extension member 10.4 represented in FIGS. 29 to 31*b*. Bone graft or other bone growth material may be packed within the circular cavity defined by the succession of rings 30.

Figure 34:
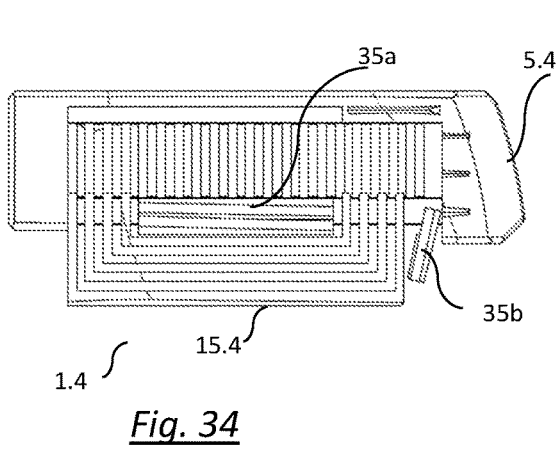
FIG. 34 represents a top view of a second variation of the cage of the fourth embodiment for an oblique approach with a deployed extension member composed of quadrilateral-shaped blades.
Figure 35:
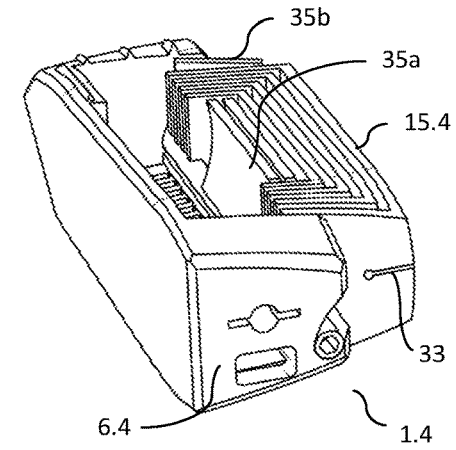
FIG. 35 represents a perspective rear view of the same cage as in FIG. 34 in the same configuration of a deployed extension member.
Figure 36A:
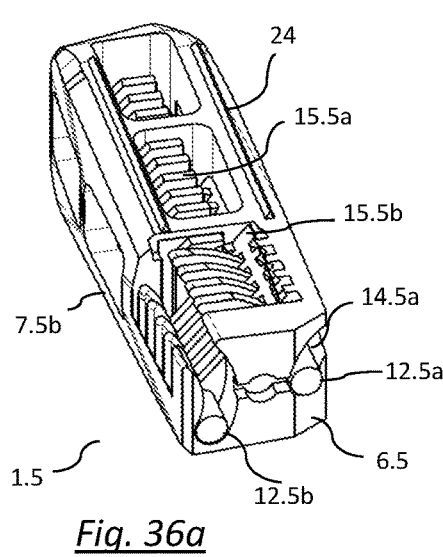
FIG. 36a represents a perspective rearview of the cage of the fifth embodiment in the first configuration of stowed blades.
Figure 37A:
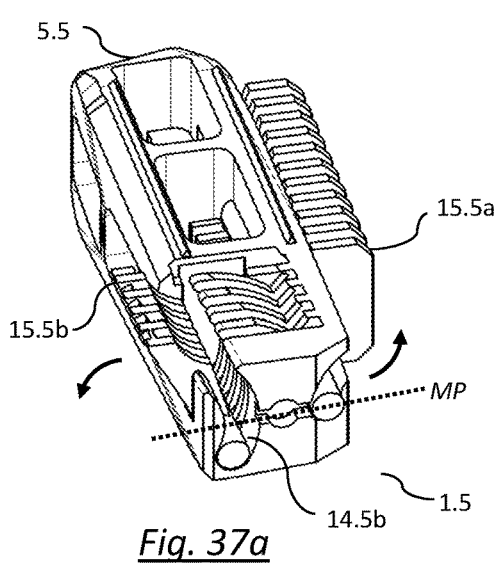
FIG. 37a represents a perspective rear view of the cage represented in FIG. 36a but in the second configuration of deployed blades.
Figure 36B:
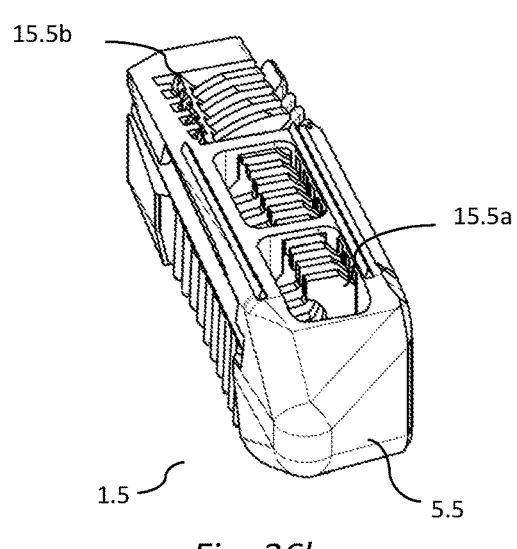
FIG. 36b represents a perspective frontal view of the same cage as in FIG. 36a in the same configuration of stowed blades.
Figure 37B:
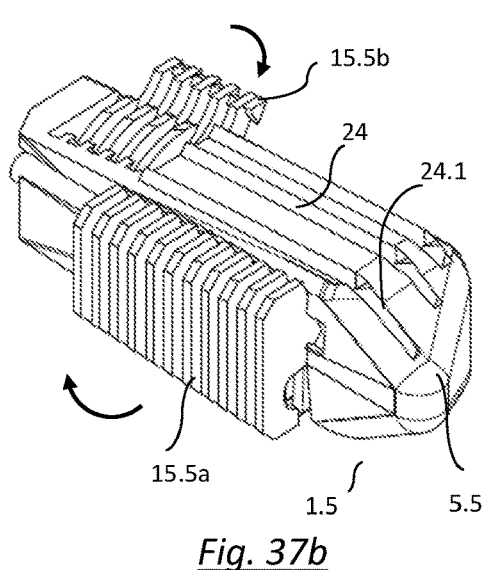
FIG. 37b represents a perspective frontal view of a variation of the cage of FIG. 37a, with extended shielding rails on the cage body and tip, in the same configuration of deployed blades.

According to FIGS. 34 and 35, a second variation of the cage 1.4 of the fourth embodiment is configured with an extension member 10.4 arranged with quadrilateral-shaped blades 15.4 connected to the base 12.4. The blades 15.4 thus define a three-sided rectangle, closed by the base 12.4. In a different variation, the blades 15.5 could be shaped in a semi-circle, like a "wolfs trap", instead of a rectangle. The extension member 10.4 also features two blades 35*a* which have a curved cross-section with a gutter profile and which are mounted on their longitudinal side on the base 12.4, and one blade 35*b* which also has a curved cross-section with a gutter profile but is fixed to the base 12.4 in an oblique acute angle. The curved blades 35*a*, 35*b* may provide some damping properties to the cage assembly 1.4.

As represented in FIGS. 30, 33, 35, 81 and 82, the planes defined by the upper surface 3.4 and lower surface 4.4 of the body 2.4 and the continuation of these planes on the bone-engaging surfaces or tranches 23.4 of the extension member 10.4 are angled obliquely so that the natural lordosis between the two vertebrae V1, V2 may be restored despite the oblique position of the cage 1.4 between the vertebrae, as shown in FIGS. 31*a* and 31*b*.

FIGS. 36*a* to 40*c* represent the cage 1.5 of the fifth embodiment, which is configured for a posterior or transforaminal approach to the spine. The width W of the body 2.5 is narrower than the width W of the bodies 2 to 2.4 of the first to fourth embodiments. According to FIGS. 36*a* to 38, similar to the cage 1.2 of the second embodiment, two extension members 10.5*a*, 10.5*b* are arranged to be slotted into two channels 14.5*a*, 14.5*b* arranged in the body 2.5, pivoting from a first configuration with stowed blades 15.5*a*, 15.5*b* to a second configuration with deployed blades. One of the channels 14.5*a* is positioned on the median horizontal plane "MP" of the body 2.5 while the other channel 14.5*b* is ex-centered from that median horizontal plane "MP" and positioned towards the lower surface 4.5 of the body 2.5. As shown in FIGS. 37*b* and 39*b*, one extension member 10.5*a* is configured with multiple parallel blades 15.5*a* having an essentially trapezoidal shape, with a circular opening 34 arranged on each of the blades 15.5*a*, for the purpose of enabling a longitudinal connecting structure 22.5 to be configured across the length of the body 2.5 to give it more stability and resistance to torque forces. As represented in FIG. 39*a*, the other extension member 10.5*b* has a shorter base 12.5*b* than the base 12.5*a* of the first extension member 10.5*a* and is arranged with narrower longitudinal blades 15.5*b*, connected together by a straight connector 20.5, whose function it is to increase the stability of the longitudinal blades 15.5*b* structure and to increase the contact surface of the bone-engaging tranche 23.5 of the blades 15.5*b* with the upper vertebra V1, especially when the straight connector 20.5 extends beyond the last blade 15.5*b* as is shown in FIGS. 38 and 39*a*. The first extension member 10.5*a* is configured to rotate approximately 180° and to engage and rest against two adjacent vertebrae V1, V2, while the second extension member 10.5*b* is configured to pivot approximately 75° and to engage and rest only against the upper vertebra V1. According to the variation represented in FIG. 37*b*, the shielding rails 24 arranged on the upper surface 3.5 and on the lower surface 4.5 of the body 2.5 have rail extensions 24.1 configured on the tip 5.5 of the body 2.5, in order to smoothen the distraction of the vertebrae V1, V2 during impactation, especially when the body 2.5 (other than the shielding rails 24 and rail extensions 24.1) is made of abrasive material.

As is shown in FIG. 40*c*, the planes defined by the upper surface 3.5 and lower surface 4.5 of the body 2.5 and the continuation of these planes on the bone-engaging tranches 23.5 of the blades 15.5*a* 15.5*b*, are angled obliquely so that the natural lordosis between the two vertebrae V1, V2 may be restored despite the oblique position of the cage 1.5 between the vertebrae. The angles of these two obliquely-configured planes for the cage 1.5 of the fifth embodiment diverge from the rear part 6.5 of the body 2.5 towards the anterior part 5.5 of the body 2.5, while, conversely, the angles of the two obliquely-configured planes described in FIGS. 30, 33, 81 and 82 for the cage 1.4 of the fourth embodiment diverge from the anterior part 5.4 of the body 2.4 towards the rear part 6.4 of the body 2.4.

FIGS. 41 and 42 represent a first variation of the cage 1.5 of the fifth embodiment, wherein one of the extension member 10.5*b* is arranged in a channel 14.5*b* also positioned ex-centrally from the horizontal median plane "MR" of the body 2.5, but towards the upper surface 3.5 of the body 2.5. The rotation required to deploy the extension member 10.5*b* of this variation is approximately 145°. The longitudinal blades 15.5*b* of this variation are also connected at their extremity by a straight connector 20.5. The advantage of the configuration of this first variation (over the extension member 10.5*b* of the cage 1.5), is that a broader perimeter of contact surface is obtained with the blades 15.5*b* to rest against the upper vertebra V1. In addition, the body 2.5 may also be arranged with more material in its bottom half portion. In yet other variations of the cage 1.5 of the fifth embodiment, a cage 1.5 may be assembled with two extension members 10.5 having the same configuration, whether configured with the shape of the extension member 10.5*a* or of the extension member 10.5*b*.

FIGS. 43, 44*a* and 44*b* represent a second variation of the cage 1.5 of the fifth embodiment, where the extension member 10.5*a* is configured with most blades 15.5*a* attached to a curved connector 31, and only three blades 15.5*a* are directly attached to the base 12.5. The advantage of this variation is to strengthen the structure of the extension member 10.5 and to enable the body 2.5 to be built with more material in its lower part.

FIGS. 45 to 49 represent a third variation of the cage 1.5 of the fifth embodiment, with a body 2.5 configured with a wedge shaped anterior part 5.5 and a succession of rectangular and parallelly arranged thin walls 28.5 defining a narrow upper surface 3.5 and a narrow lower surface 4.5 of the body 2.5 and comparatively high lateral sides 7.5*a*, 7.5*b*. The thin walls 28.5 and the anterior part 5.5 are all fixed to a longitudinal connecting structure 22.5. Multiple parallel thin hooks 21.5 are mounted on the extension member 10.5 and are arranged to be slotted within the slits 9.5 between the thin walls 28.5, in the first configuration of the cage 1.5 with a stowed extension member 10.5. The cage 1.5 of this variation is designed to be introduced between two vertebrae V1, V2 with its lateral sides 7.5*a*, 7.5*b* engaging the two vertebrae. When the cage is in its desired position, it is rotated 90°. As shown in FIG. 48, during such rotation, the extension member 10.5 may be pivoted to deploy the hooks 21.5. When the hooks 21.5 are fully deployed, their upper and lower bone-engaging tranches 23.5 rest against the vertebrae V1, V2 and increase the width W from the narrow surfaces 3.5, 4.5 of the body 2.5 to the larger width W1 of the whole cage 1.5.

Figure 50:
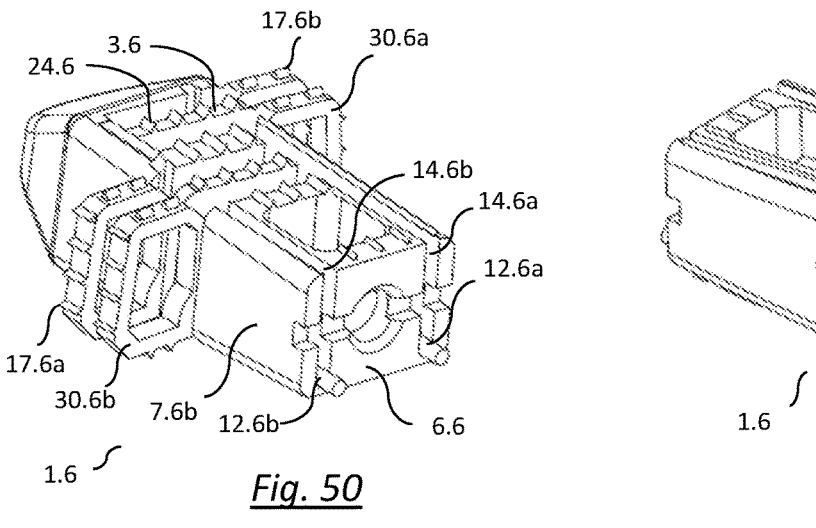
FIG. 50 represents a perspective rearview of the cage of the sixth embodiment in the second configuration of two sets of deployed rings.
Figure 51:
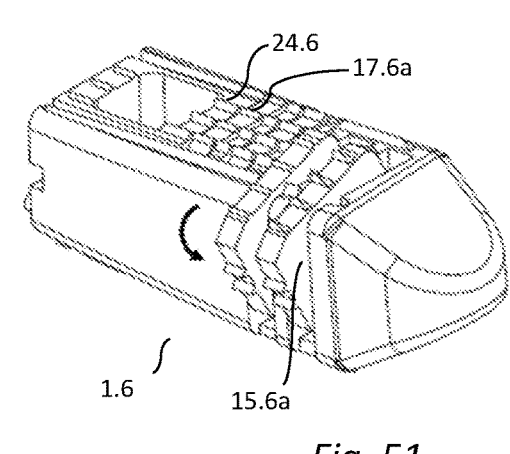
FIG. 51 represents a perspective frontal view of the cage of the sixth embodiment with one deploying set of two blades.
Figure 52:
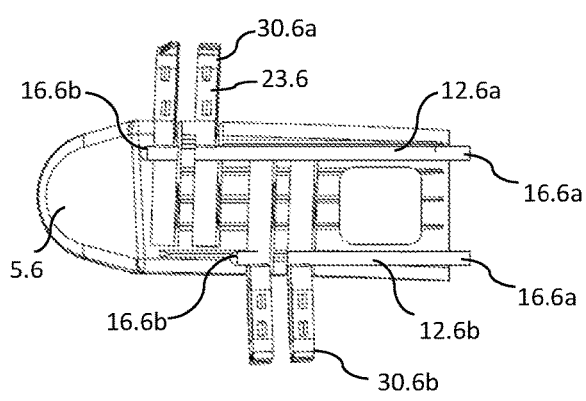
FIG. 52 represents a top view of the cage of FIG. 50.

FIGS. 50 to 54 represent the sixth embodiment of the invention, consisting of a cage assembly 1.6 of a body 2.6 configured to receive two extension members 10.6*a*, 10.6*b*, each arranged with one set of two parallel rings 30.6*a*, 30.6*b*. As shown in FIGS. 50, and 52, the bases 12.6*a*, 12.6*b* of said extension members 10.6*a*, 10.6*b* are configured as rods to be received through two straight channels 14.6*a*, 14.6*b* arranged in the body 2.6. The bottom of the two straight channels 14.6*a*, 14.6*b* are configured in same plane, towards the lower surface 4.6 of the body 2.6. The base 12.6*b* of one extension member 10.6*b* is shorter than the base 12.6*a* of the other extension member 10.6*a*, and its set of blades 15.6*b* or rings 30.6*b* deploys closer to the rear part 6.6 of the body 2.6.

Figure 53:
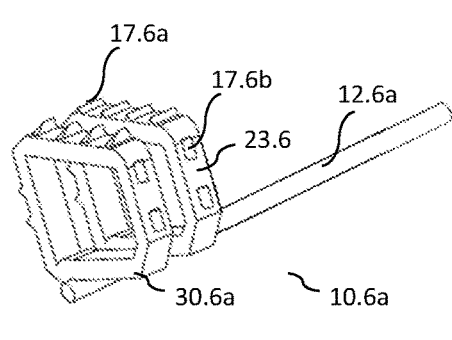
FIG. 53 represents a perspective frontal view of an extension member of the cage of the sixth embodiment with one set of two rings.

According to FIGS. 50 to 52 and 54, the upper surface 3.6 and the lower surface 4.6 of the body 2.6 of the cage 1.6 are arranged with short sections of shielding rails 24.6 configured in the longitudinal axis of the body 2.6. As also shown in FIG. 53, the tranches of the rings 30.6*a*, 30.6*b* of the extension member 10.6 are covered with thin rails 17.6*a*, 17.6*b*: more specifically, the thin rails 17.6*a* on one tranche of the rings 30.6*a*, 30.6*b* are arranged in the longitudinal axis of the body 2.6, while the thin rails 17.6*b* on the two bone-engaging tranches 23.6 of each of the rings 30.6*a*, 30.6*b* are arranged perpendicular to the longitudinal axis of the body 2.6. According to FIG. 51, when the cage 1.6 is in its first configuration with stowed rings 30.6*a*, 30.6*b*, the thin rails 17.6*a* on the tranche of the rings 30.6*a*, 30.6*b* form a continuity with the small sections of shielding rails 24.6 on the upper and lower surfaces 3.6, 4.6 of the body 2.6. This enables the vertebrae V1, V2 to be shielded from the body 2.6 of the cage 1.6 by "reconstructed" continuous shielding rails composed by a succession of thin rails 17.6*a* and small sections of shielding rails 24.6. As shown in FIGS. 50 and 52, when the extension members 10.6*a*, 10.6*b* are rotated and the rings 30.6*a* or blades 15.6*a* are deployed, the continuity of the thin rails 17.6*a* with the small sections of shielding rails 24.6 is interrupted, and the small sections of shielding rails 24.6 thus become anchoring means preventing the migration of the cage 1.6 both in the longitudinal axis and in the lateral axis, while the thin rails 17.6*a* serve no longer any purpose. However, the thin rails 17.6*b* on the two bone engaging tranches 23.6 of the rings 30.6*a*, 30.6*b* or blades 15.6*a*, 15.6*b* which now rest into the vertebrae V1, V2, serve as anchors for the cage 1.6 and also prevent its migration in both the longitudinal and lateral axes; the invention thus enables to move from a first configuration with stowed extension members 10.6*a*, 10.6*b* which is protective of the vertebrae V1, V2 during insertion, to becoming effective anchoring means in the second configuration of the cage 1.6, after the deployment of the extension members 10.6*a*, 10.6*b*.

The cage 1.6 of the sixth embodiment may deploy both extension members 10.6*a*, 10.6*b* or only one of them, depending on the anatomy between the two vertebrae V1, V2. Also, in another variation of deployment, two cages 1.6 may be introduced and positioned side by side between two vertebrae V1, V2, with the first cage deploying one extension member 10.6*a* towards the second cage 1.6 and that second cage deploying one extension member 10.6*b* towards the first cage: in that configuration, given the shorter extension member 10.6*b*, the respective sets of rings 30.6 or blades 15.6 of both deployed extension members, each deployed from one separate cage, are positioned parallel to each other and create a continuity of four rings 30.6 or blades 15.6 and extend the support surface between the two cages 1.6 in the way of a bridge, to share the load of the deployed cages with the vertebrae V1, V2.

According to FIGS. 55*a* to 55*f*, because their bases 12.6*a*, 12.6*b* are positioned longitudinally on the same plane, the extension members 10.6*a*, 10.6*b* of the cage 1.6 are pivoting in opposite directions and their rings 30.6*a*, 30.6*b* are deploying in opposite directions. As shown in FIGS. 55*a* to 55*c*, the first set of rings 30.6*a* deploys according to the same process as the cage 1 of the first embodiment, as described in FIGS. 18*a* to 18*c*. According to FIG. 55*d*, the body 2.6 of the cage 1.6 is then rotated in the reverse direction to the one represented in FIG. 55*b* and the base 12.6*b* of the second extension member 10.6*b* is then pivoted in the opposite direction to enable the deployment of the second set of rings 30.6*b*, which process is represented in FIGS. 55*d* to 55*f*.

Figure 54:
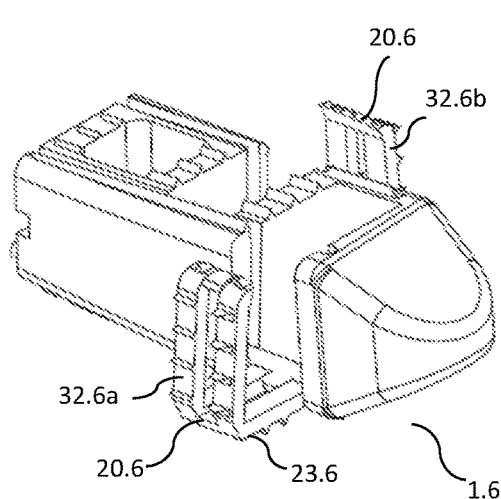
FIG. 54 represents a perspective frontal view of a variation of the cage of the sixth embodiment in the second configuration of deployed "L" shaped extension members.

FIG. 54 describes a variation of the sixth embodiment of the cage 1.6 with extension members 10.6*a*, 10.6*b* each configured to deploy one set of two "L"-shaped extensions 32.6*a*, 32.6*b* instead of blades 15, hooks 21 or rings 30. The "L"-shaped extensions 32.6*a*, 32.6*b* rest against one vertebra with the bone-engaging tranches 23.6 of the "L"-shapes, and against the other vertebra with the tips of the other legs of the "L"-shapes; such tips are connected by a straight connector 20.6, increasing the load sharing surface of such tips.

Figures 56, 57, 58A, 58B, 59, 60A, 60B, 61:
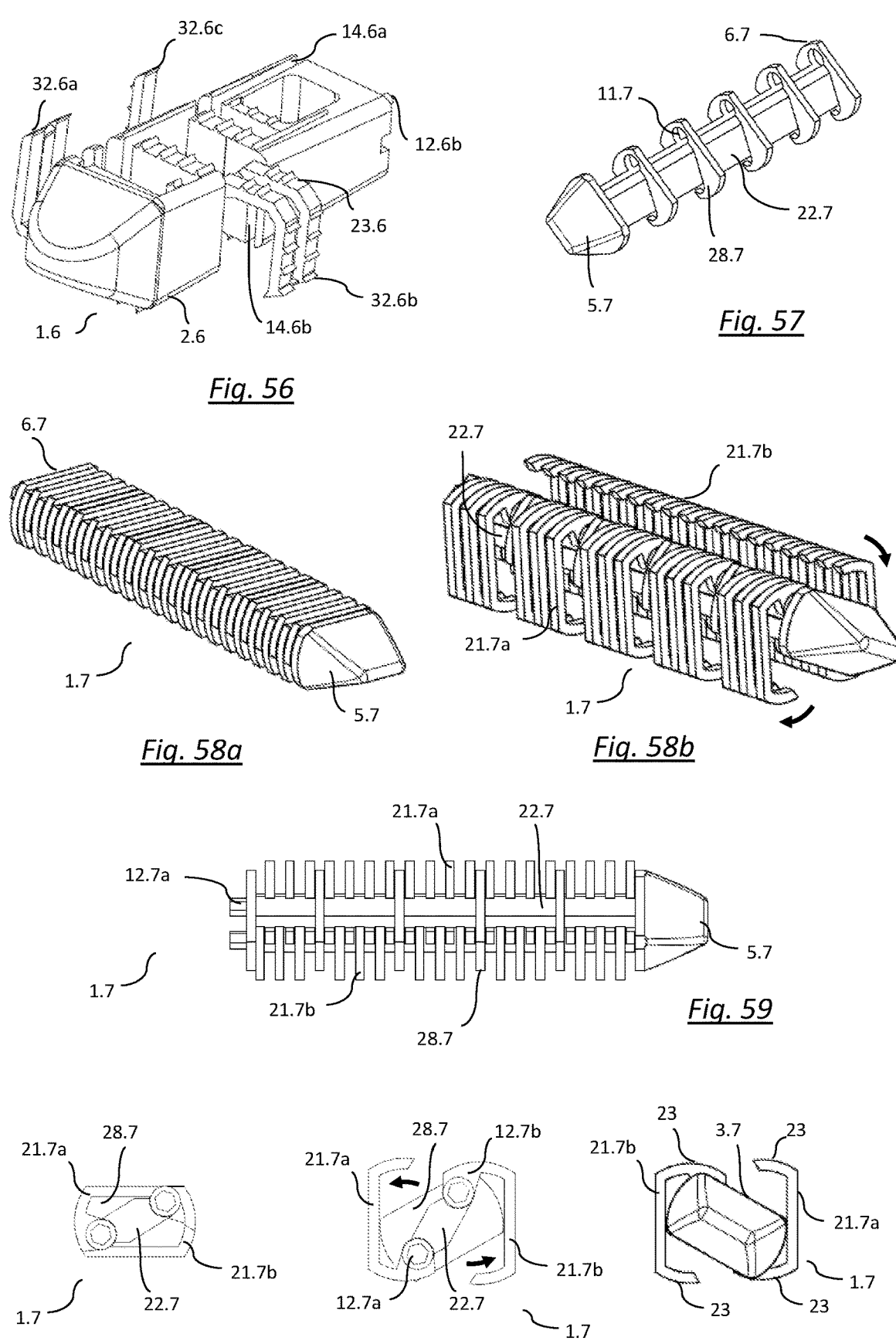
FIG. 56 represents a perspective frontal view of another variation of the cage of the sixth embodiment with two diagonally positioned "L" shaped extension members.
FIG. 57 represents a perspective frontal view of the body of the cage of the seventh embodiment.
FIG. 58a represents a perspective frontal view of the cage of the seventh embodiment with two diagonally positioned extension members in a stowed configuration.
FIG. 58b represents a perspective frontal view of the same cage as in FIG. 58a with two fully deployed sets of hooks.
FIG. 59 represents a top view of the same cage as in FIG. 58b with two fully deployed sets of hooks.
FIG. 60a represents a lateral cross-section viewed from the rear of the cage of FIG. 58a in the first configuration with two sets of stowed hooks.
FIG. 60b represents the same lateral cross-section view as in FIG. 60a of the cage represented in FIGS. 58b and 59, but with fully deployed hooks.
FIG. 61 represents a frontal view of the cage represented in FIGS. 58b, 59 and 60, with fully deployed hooks.

In another variation of the sixth embodiment represented in FIG. 56, the body 2.6 of the cage 1.6 receives two extension members 10.6*a*, 10.6*b*, with their bases 12.6*a*, 12.6*b* positioned diagonally from each other. The first channel 14.6*a* opens on the upper surface 3.6 and has its bottom close to the lower surface 4.6 and the second channel 14.6*b* opens on the lower surface 4.6 and has its bottom close to the upper surface 3.6 of the body 2.6. These diagonally opposed extension members 10.6*a*, 10.6*b* are rotated in the same direction for the deployment of their "L"-shaped extensions 32.6*a*, 32.6*b*, 32.6*c*, according to the process described in FIGS. 18*a* to 18*c*. In addition, one extension member 10.6*a* is configured with one set of two "L"-shaped extensions 32.6*a* and one individual "L"-shaped extension 32.6*c*, while the other extension member 10.6*b* is configured only with one set of two "L"-shaped extensions 32.6*b*. This variation of the cage 1.6 demonstrates the multiple options for configuring the extension members 10.6 with a variety in the choice, numbers and positioning of blades 15, hooks 21, rings 30, "L"-shaped extensions 32.6 or any other shape.

FIGS. 57 to 61 represent the seventh embodiment of the invention, comprising a cage 1.7 with a body 2.7 configured to receive two obliquely positioned extension members 10.7*a*, 10.7*b*, each with multiple hooks 21.7*a*, 21.7*b* mounted on its base 12.7*a*, 12.7*b*. As shown in FIG. 57, in this embodiment, fewer thin walls 28.7 are arranged on a connecting structure 22.7 to leave room for a greater number of foldable hooks 21.7*a*, 21.7*b* to fit in the longitudinal dimension of the body 2.7. The thin walls 28.7 are pierced by round openings 11.7 to receive the bases 12.7*a*, 12.7*b* of the extension members 10.7*a*, 10.7*b*. On large portions of the cage 1.7, the two opposing sets of hooks 21.7*a*, 21.7*b* are directly adjacent to each other. The connecting structure 22.7 connects the thin walls 28.7 to the rear part 6.7 and to the anterior part 5.7 of the body 2.7. As shown in FIGS. 58*a* and 60*a*, the tranches of the two sets of hooks 21.7*a*, 21.7*b* in the stowed configuration constitute most of the outer surfaces of the cage 1.7.

FIGS. 60*b* and 61 describe how, in the deployed configuration of the cage 1.7, unlike with all other embodiments of the invention, the volume of the cage 1.7 is only defined by the hooks 21.7*a*, 21.7*b* of the deployed extension members 10.7*a*, 10.7*b* and the contact surface of the cage 1.7 with the vertebrae V1, V2 is only defined by the perimeter of the bone-engaging tranches 23 of the hooks 21.7*a*, 21.7*b*, and not by any part of the body 2.7. Thus, in its deployed configuration, the cage 1.7 of the seventh embodiment of the invention represents another reflection of a scaffold nature of the invention, with the body 2.7 serving as a vector of deployment of the cage 1.7, as structural support for the extension members 10.7*a*, 10.7*b*, as connector between the anterior part 5.7 and rear part 6.7 of the body 2.7 and as means of locking for the extension members 10.7*a*, 10.7*b*. Due to this characteristic, the additional specificity of this cage 1.7, is that its delivery between the two vertebrae V1, V2, does not require a reverse-rotation of the body 2.7 (as is otherwise shown in FIG. 18*c* for the first embodiment and in FIG. 55*e* for the sixth embodiment). In fact, the extension members 10.7*a*, 10.7*b* of the cage 1.7 may even be deployed without rotation of the body 2.7 at all, as the deployment of the hooks 217*a*, 217*b* may on their own create a lever effect to distract the vertebrae V1, V2.

The cage 1.7 of this seventh embodiment more than doubles its volume in height and width (but mostly in height) from the stowed configuration represented in FIGS. 58*a* and 60*a*, to the deployed configuration represented in FIGS. 58*b*, 59, 60*b* and 61.

While the cage 1.7 of the seventh embodiment as described in FIGS. 57 to 61 may self-lock in the deployed configuration, any additional locking means may be configured on the cage 1.7, such as a rack-and-pinion system, or the introduction of a locking pin after deployment, or the slight retraction or rotation of a pre-mounted pin. With such a locking mechanism, the cage 1.7 may also be deployed with its body 2.7 positioned at 90° compared to its position represented in FIGS. 60*b* and 61, in which case the hooks 21.7*a*, 21.7*b* will rest against the vertebrae V1, V2 with other tranches than the bone-engaging tranches 23 represented in FIG. 61. In this variation, the method of delivery of the cage is different as well: the cage is inserted, a 90° rotation is actuated on the body 2.7, and the extension members 10.7*a*, 10.7*b* are deployed outwards according to the method of the invention.

FIGS. 62 to 64 describe the eighth embodiment of a cage 1.8 configured with two extension members 10.8*a*, 10.8*b*, with the axes of their respective bases 12.8*a*, 12.8*b* both positioned in a plane which is essentially parallel to the upper surface 3.8 of the body 2.8, near such upper surface 3.8. The body 2.8 of the cage 1.8 has an oblong tip 5.81 which is positioned obliquely and may be used to distract the vertebrae V1, V2 for the insertion of the cage 1.8 between the vertebrae V1, V2, by pivoting the body 2.8 according to the method described in FIGS. 37a and 37b of U.S. Ser. No. 15/739,696. The extension members 10.8*a*, 10.8*b* comprise parallelly arranged sets of triangular blades 15.8*a*, 15.8*b* which are stowed within the body 2.8 in a first configuration shown in FIG. 62 and are both deployed beyond the upper surface 3.8 of the body 2.8, and beyond the lateral sides 7.8*a* and 7.8*b*, as shown in FIGS. 63 and 64. After the cage 1.8 has been inserted between the vertebrae V1, V2 according to FIG. 37*b* of U.S. Ser. No. 15/739,696, and is in its final position, the first extension member 10.8*b* is deployed, and its blades 15.8*b* deploy beyond the lateral side 7.8*b* of the body 2.8 in the same way as represented in FIGS. 55*b* and 55*c* for the cage 1.6 of the sixth embodiment. As shown in FIGS. 63 and 64, the blades 15.8*b* are locked in a deployed configuration beyond the lateral side 7.8*b* and beyond the upper surface 3.8 of the body 2.8. The body 2.8 of the cage 1.8 is then reverse-rotated in the same way as represented in FIG. 55*d* for cage 1.6 whereupon the second extension member 10.8*a* may be pivoted to deploy its set of parallel blades 15.8*a*. FIG. 63 represents this step for cage 1.8, when the first extension member 10.8*b* is fully deployed and the second extension member 10.8*a* is in its course of deployment.

In this eighth embodiment, in contrast to what is described in FIG. 55*d* for cage 1.6, the upper surface 3.8 of the body 2.8 does not engage the upper vertebra V1: it is the deployed extension member 10.8*b* only, with the bone-engaging tranches 23 of the blades 15.8*a*, which engages the upper vertebra V1 as lever to distract both vertebrae V1, V2 in order to then deploy the second extension member 10.8*a*. The advantage of the cage 1.8 of the eighth embodiment, as represented in FIG. 64, is that the cage 1.8 may be expanded both laterally beyond the two lateral sides 7.8*a*, 7.8*b* and in height, beyond the upper surface 3.8.

FIGS. 65 to 69*b* describe a ninth embodiment of the invention, in which the cage 1.9 comprises one body 2.9 and one extension member 10.9, wherein the bottom of the channel 14.9 is positioned in the central longitudinal axis ua between the two lateral sides 7.9*a*, 7.9*b* of the body 2.9. The body 2.9 has one lateral side 7.9*a* with a higher height than the height of the other lateral side 7.9*b*. The extension member 10.9 comprises a base 12.9 configured with blades 15.9.

The cage 1.9 is delivered according to the method described in U.S. Pat. No 9,421,114 by an instrument 40 shown in FIG. 65. A first handle 41*a* and a second handle 41*b* are mounted on the instrument 40. A rod is fixed to the first handle 41*a* at the proximal end of the rod and is configured to engage the proximal end 16*a* of the extension member 10.9 to actuate its pivoting, according to the relevant steps of the method of deployment of the invention. The first rod fixed to the first handle 41 *a* is slid inside of the second rod mounted to the second handle 41*b*. The second handle 41 *b* may rotate the cage body 2.9 according to the delivery methods of the inventions. At its distal end, the instrument 40 is configured with two extensions 42*a*, 42*b* which have a gutter cross-section, as shown in FIGS. 65, 66*a* to 66*c*. The two extensions 42*a*, 42*b* of the instrument 40 may be slid into two respective curved receiving slits 43*a*, 43*b* arranged on the lateral sides 7.9*a*, 7.9*b* and/or on the upper surface 3.9 and/or lower surface 4.9 of the body 2.9 of the cage 1.9, such curved receiving slits matching the gutter cross-section of the two extensions 42*a*, 42*b*.

The advantage of these gutter-shaped extensions 42*a*, 42*b* is that their corresponding curved receiving slits 43*a*, 43*b* in the body 2.9 do not take up much space, leaving more material to secure the stability of the body 2.9 and also maximizing the size of the extension member 10.9 and of the blades 15.9, in contrast to the footprint of extensions with different cross-sections. In addition, the pairing of curved receiving slits 43*a*, 43*b* with the curved extensions 42*a*, 42*b* eliminates or greatly limits the risk of separation of the two extensions 42*a*, 42*b* beyond the dimension "D". In addition, as shown in FIGS. 66*a* to 66*c*, this curved cross-section of the extensions 42*a*, 42*b*, enables one same instrument 40 with extensions 42*a*, 42*b* separated by the same dimension "D" to match the same degrees of curved slits 43*a*, 43*b* arranged on different sizes of bodies 2.9 of cages 1.9, while still serving their purpose of the delivery technique. This is advantageous as it limits the number of instruments 40 needed to deliver multiple sizes of cages. According to FIGS. 66*a* to 66*c*, the two extensions 42*a*, 42*b* are arranged in opposed curves; in variations of the instrument 40, these extensions 42*a*, 42*b* may have curves facing the same direction, or curves with their convex portions facing different axes. The instrument 40 with its extensions 42*a*, 42*b*, may also be used on interbody cages which are not the subject matter of this invention, such as single block interbody cages or other types of expandable cages.

Figure 67C:
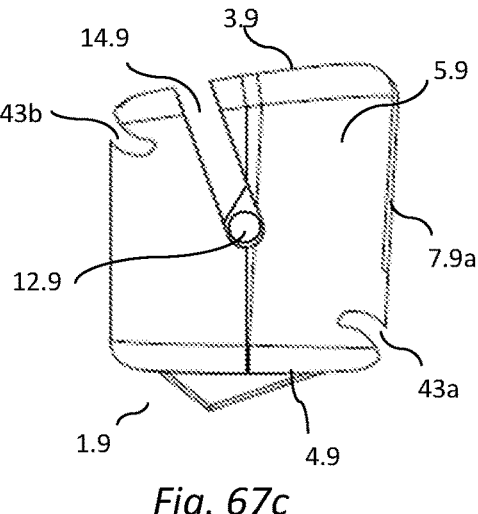
FIG. 67c represents a frontal view of the cage represented in FIGS. 67a and 67b with one extension member in stowed configuration.
Figure 68C:
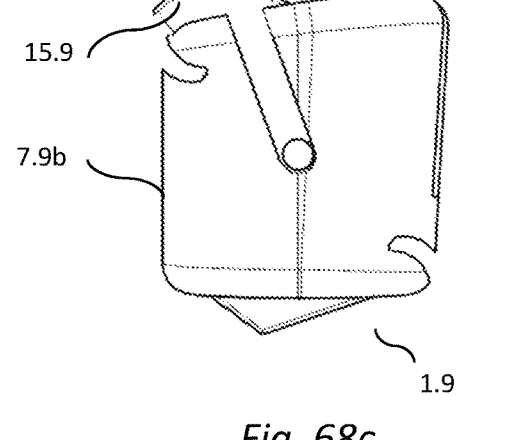
FIG. 68c represents a frontal view of the cage represented in FIGS. 68a and 68b with its deployed extension member.

FIGS. 67*a*, 67*b* and 67*c* represent how in the first configuration of the cage 1.9 of the ninth embodiment, the blades 15.9 are stowed in the body 2.9 within slits 9.9 configured in the thickness of one lateral side 7.9*a*. When deployed in the second configuration, the blades 15.9 increase both the width and the height of the cage 1.9 by leveling the upper surface 3.9 to plane "F", as shown in FIG. 68*c*.

Figure 69A:
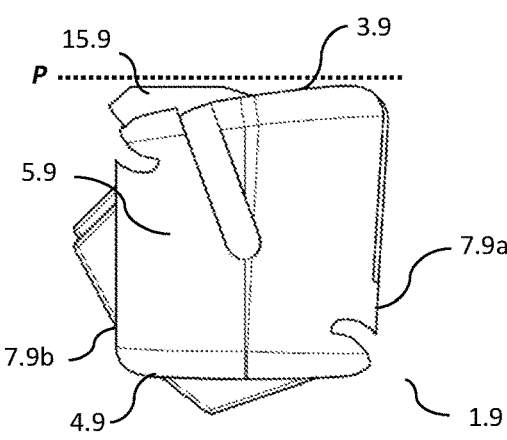
FIG. 69a represents a frontal view of the cage of a variation of the cage of the ninth embodiment with an extension member deployable through the upper surface or lateral side of the body, in the configuration deployed through the upper side.
Figure 69B:
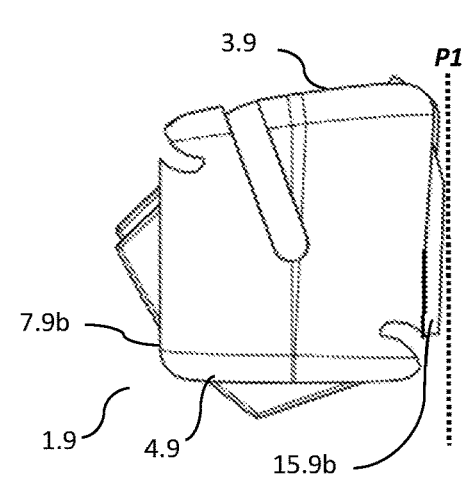
FIG. 69b represents a frontal view of the same cage as in FIG. 69a in the configuration of deployed extension member through one lateral side of the body.
Figure 70:
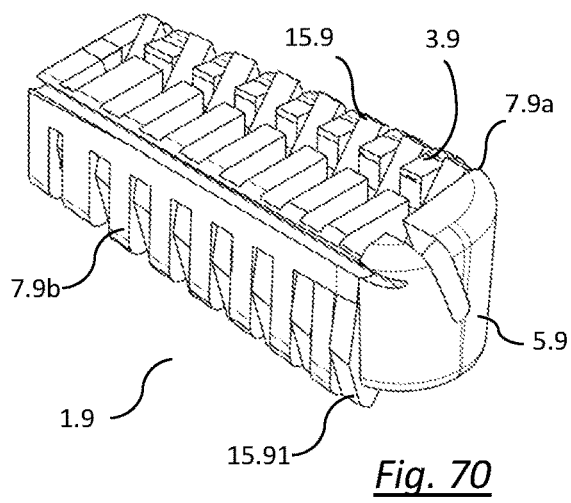
FIG. 70 represents a perspective frontal view of the second variation of the cage of the ninth embodiment with a single extension member arranged with a twin set of opposing blades, in stowed configuration.

FIGS. 69*a* and 69*b* represent a variation of the cage 1.9 of the ninth embodiment, where the body 2.9 is configured to enable the lateral sides 7.9*a*, 7.9*b* to become the surfaces of the body 2.9 resting against the upper and lower vertebrae V, V2. Depending upon the anatomy of the vertebral segment and the space between the two vertebrae V1, V2, the surgeon may choose to deploy the blades 15.9 through the upper surface 3.9 to create plane "P" (as shown in FIG. 69*a*) or to rotate the cage of 90° and to deploy the blades 15.9 through the lateral side 7.9*a* to create plane "P1" (as shown in FIG. 69*b*) with the lateral sides 7.9*a*, 7.9*b* now serving as upper and lower contact surfaces of the body 2.9 and the vertebrae V1, V2.

Figure 71:
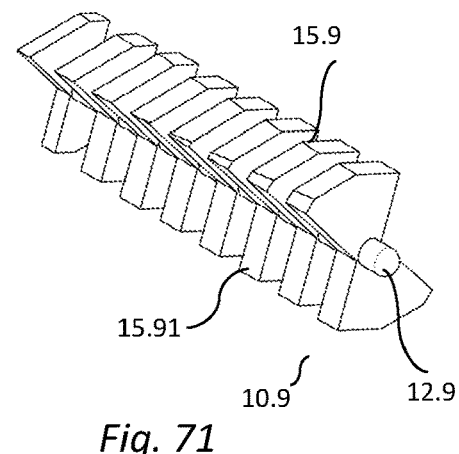
FIG. 71 represents a perspective frontal view of the extension member with a twin set of opposing blades of the cage represented in FIG. 70.
Figure 72A:
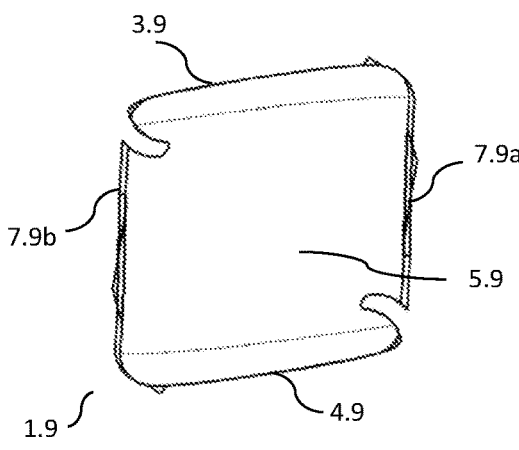
FIG. 72a represents a frontal view of the cage represented in FIG. 70 in the configuration of stowed extension member with a twin set of opposing blades.
Figure 72B:
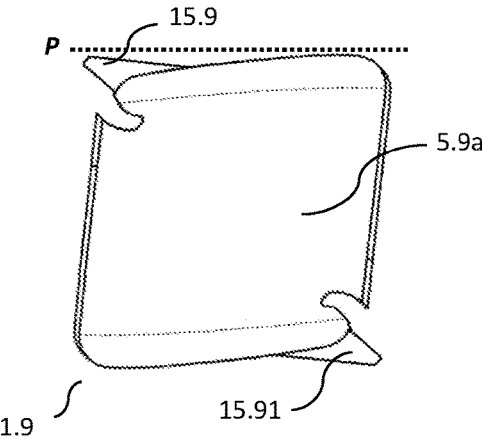
FIG. 72b represents a frontal view of the same cage as in FIGS. 70 and 72a in the configuration of deployed extension member with a twin set of opposing blades.

FIGS. 70 to 72*b* represent another variation of the cage 1.9 of the ninth embodiment, with a body 2.9 configured to receive one single extension member 10.9 on its central longitudinal axis "α1" arranged with one twinset of symmetrically opposed blades 15.9, 15.91 (shown in FIG. 71). Both lateral sides 7.9*a*, 7.9*b* of the body 2.9 are arranged with slits 9.9 alternating with walls 8.9 to stow the blades 15.9, 15.91 of the extension member 10.9 in the stowed configuration of the cage 1.9 represented in FIGS. 70 and 72*a*. This feature doubles the gain in height of the cage 1.9 in the second configuration of deployed blades 15.9, 15.91, as shown in FIG. 72*b* compared to the height gained by the deployed blades 15.9 of the other variation of the cage 1.9 shown in FIG. 68*c*.

Figure 73:
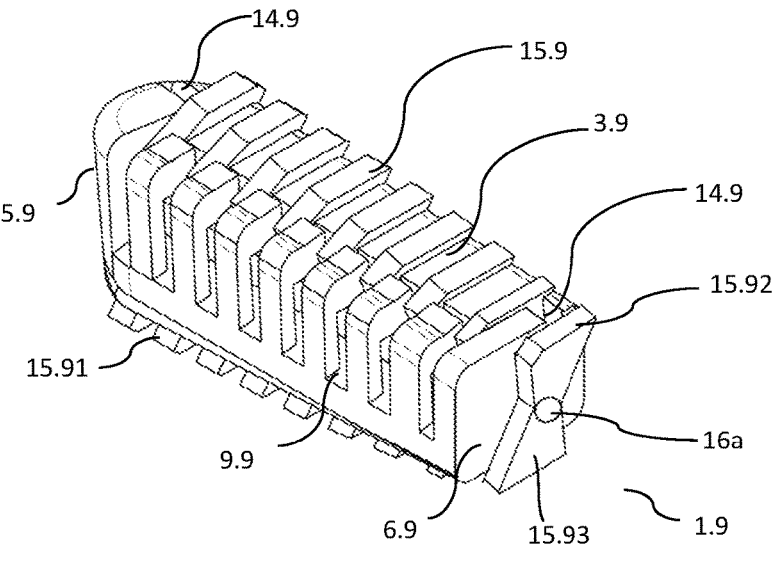
FIG. 73 represents a perspective rear view of third variation of the cage of the ninth embodiment with a single extension member with additional twin blades arranged beyond the rear part of the body of the cage.

FIG. 73 describes another variation of the cage 1.9 of the ninth embodiment, where the extension member 10.9 may have its last set of twin blades 15.92, 15.93 slotted within the channel 14.9 beyond the rear part 6.9 of the body 2.9. The advantage of this variation is that the same body 2.9 may be used to receive extension members 10.9 within its channel 14.9 which may be longer than the body 2.9 itself. The invention is thus fully modular, as it enables to vary the height, length, width, angles and overall shape of the cage 1.9 by mounting different types of extension members 10.9 on the same body 2.9, to accommodate the needs of a particular anatomy.

FIGS. 83 to 85 represent a tenth embodiment of a cage 1.10 configured with a cylindric shaped body 2.10 arranged with a succession of parallel disc shaped thin walls 28.10 and slits 9.10, the thin walls and anterior part 5.101 of the body 2.10 being connected by one or more connecting structures 22.10. The anterior part 5.10 of the body 2.10, is arranged with a tip 5.101 having two concave slopes to be inserted between two vertebrae V1, V2. The extension member 10.10 is configured with flat-sided hooks 21.10 parallelly mounted on a base 12.10 for a full deployment after pivoting of approximately 72°. The cage 1.10 is inserted between two vertebrae by first inserting the tip 5.101, then pivoting the body 2.10 or cage 1.10 of 90° in order to distract the vertebrae up to a dimension close to the height of the body 2.10, and then pushing the cage 1.10 into is final position between the vertebrae V1, V2. The body 2.10 of the cage 1.10 may also be configured with threads arranged on the periphery of the cylindric thin walls 28.10 of the body 2.10 so that the cage 1.10 may be screwed into position according to a well-known delivery method of interbody cages.

The advantage of the cage 1.10 of this tenth embodiment is thus to offer an extension member 10.10 of the invention on a cylindric-shaped body 2.10, which is either impactable, or screwable. Another advantage is that after the insertion of the cage 1.10, there is no need to distract the vertebrae V1, V2 by pivoting the body 2.10 according to the methods of the inventions, because the hooks 21.10 are slid out of the slits 9.10 arranged in the body 2.10 by a simple pivoting of the extension member 10.10. Preferably, the deployment of the extension member 10.10 is actuated in a position of the cage 1.10 relative to the vertebrae V1, V2 where the base 12.10 of the extension member 10.10 and round openings 11.10 of the body 2.10 are close to the upper or lower vertebra V1, V2.

Figure 86:
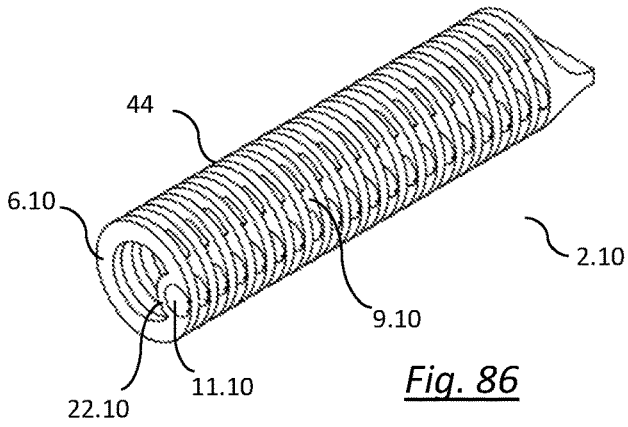
FIG. 86 represents a perspective rear view of the cylindric-shaped body of a variation of the body of the tenth embodiment configured with a set of parallel rings.
Figure 87:
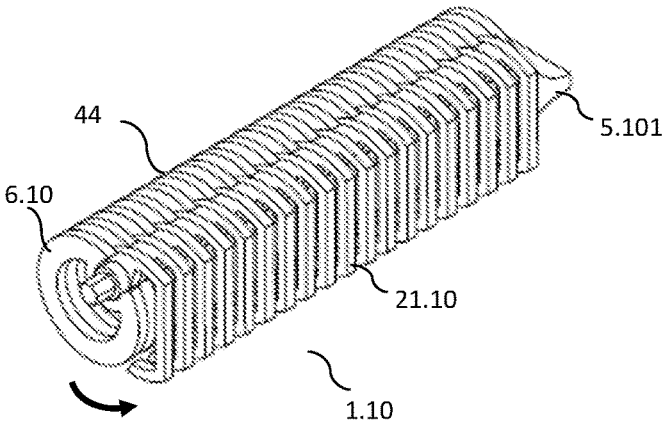
FIG. 87 represents a perspective rear view of a variation of the cage of the tenth embodiment with the body represented in FIG. 86 and with its deployed extension member arranged with flat-sided hooks.
Figure 88:
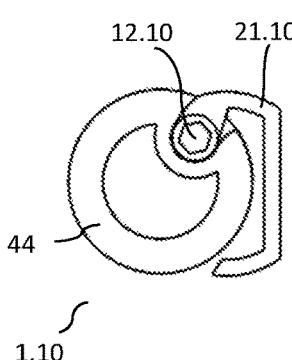
FIG. 88 represents a rear view of the cage represented in FIG. 87 with a cylindric shaped body and deployed extension member with flat-sided hooks.

In variations of this tenth embodiment represented in FIGS. 86 to 89, the thin disc-shaped walls 28.10 of the body 2.10 may be replaced by a succession of parallel rings 44, creating a tubular structure of rings 44, as shown in FIG. 86. The configuration of rings 44 on the body 2.10 and hooks 21.10 on the extension member 10.10 is advantageous for packing graft material and enabling its growth through the rings 44 and hooks 21.10. As shown in FIGS. 87 and 88, the hooks 21.10 are flat-sided in order to reduce the lateral protrusion of material which does not rest against the vertebrae V1, V2.

Figure 89:
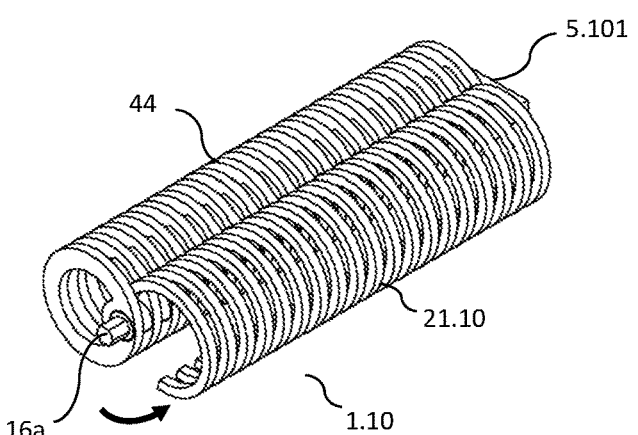
FIG. 89 represents a perspective rear view of another variation of the cage of the tenth embodiment with a body comprising of a set of parallel rings, with a deployed extension member arranged with cylindric-shaped hooks.
Figure 90:
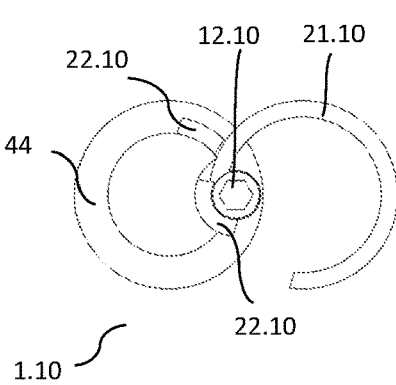
FIG. 90 represents a lateral cross-section of the cage represented in FIG. 89 viewed from the rear with a cylindric shaped body and deployed extension member arranged with cylindric-shaped hooks.

FIGS. 89 and 90, in contrast, describe a variation of the tenth embodiment, where the extension member 10.10 is arranged with a succession of cylindric-shaped hooks 21.10. According to FIG. 89, the advantage of this variation is that the width "W" of the cage 1.10 with deployed circular hooks 21.10 is wider than the width "W" of the cage 1.10 of the other variation shown in FIG. 88. Preferably, the deployment of the extension member 10.10 of this variation is first actuated in a position of the cage 1.10 relative to the vertebrae where the base 12.10 of the extension member and the circular openings 11.10 of the body 2.10 are close to the upper or lower vertebra V1, M2. As the extension member 10.10 is gradually deployed, the body 2.10 may be pivoted to gradually bring the position of the base 12.10 and channel 14.10 towards a more central position between the upper and lower vertebrae until the full deployment is complete, as shown in FIG. 90.

This tenth embodiment again illustrates the scaffolding characteristics of the invention, of first stowing and then unfolding multiple thin scaffolds to create a solid cage 1.10 structure.

FIGS. 91 to 94 describe the eleventh embodiment of the invention, consisting of an inter-spinous vertebral implant 1.11 configured to be inserted between two adjacent spinous processes V1, V2 to maintain them apart. According to FIG. 91, the implant 1.11 of the seventh embodiment described in FIGS. 58*a* to 61 may be used to separate the vertebrae V1, V2 at the spinous process level. FIG. 92 shows the same segment of spinous processes V1, V2 after the deployment of the implant 1.11. In a variation shown in FIG. 93, the implant 1.11 is configured with one extension member 10.11*a* arranged with one or more hooks 21.11*a* designed to expand the space between the vertebrae, while the other extension member 10.11*b* is arranged with two hooks 21.11*b* to deploy beyond the surfaces of the spinous processes in order to secure the implant against forwards or backwards motions. In a second variation of the eleventh embodiment represented in FIG. 94, the implant 1.11 is configured with one single extension member 10.11*a* configured with two functional features: one lever 45, designed to expand the distance between the body 2.11 of the implant 1.11 and the lower vertebra V2 and one or two hooks 21.11 to prevent the migration of the implant 1.11.

All eleven embodiments and their variations of the cage 1, or of the body 2 or of the extension member 10 individually, may be structured to allow a dampening effect of the cage 1 or of some of its individual components when submitted to the compression force of the vertebrae V1, V2 or other motion forces. Soft cages which mimic the cancellous bone structure of vertebral plates prevent subsidence and promote bone growth. Implants with dampening features are also beneficial for extra-discal implants such as inter-spinous implants, as they protect the bone structure of the spinal processes.

As shown in FIGS. 78 and 79 for the cage 1.2 of the second embodiment, in FIG. 27 for the cage 1.3 of the third embodiment, in FIGS. 34, 35 and 80 to 82 for the cage 1.4 of the fourth embodiment and in FIGS. 45 to 49 for the cage 1.5 of the fifth embodiment, thin walls 28, 28.2, 28.4, 28.5 arranged on a body 2.2, 2.3, 2.42.5 inherently have a more flexible structure than larger walls 8 (such as those shown in FIGS. 1 and 2) depending also on the choice of material.

Curved thin walls, which are similar in structure to the curved blades 35*a*, 35*b* represented in FIGS. 34 and 35, which have a cross-section shaped as a gutter, may also enhance the flexibility of the cage. The flexibility of the thin walls 28, 28.2, 28.4, 28.5 may also be increased by arranging notches 27 on the tranches of the thin walls 28.2, 28.4, 28.5: either on their tranches engaging the vertebrae as shown in FIGS. 45, 48 and 49 or on the tranches of the thin walls 28.2, 28.4, 28.5 defining the lateral sides 7.2*a*, 7.2*b*, 7.5*a*, 7.5*b* of the body 2.2, 2.4, 2.5 (such as shown in FIGS. 78, 79, 81 and 82). These notches 27 may be arranged perpendicular to the tranche or obliquely; they may also be curved.

Figure 74:
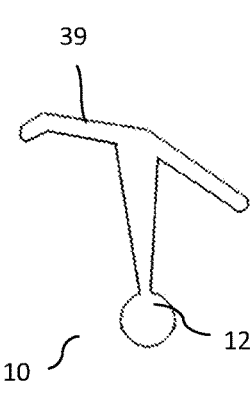
FIG. 74 represents a cross-section of a "T"-shaped extension member.

Another flexibility-enhancing feature is to arrange slits 33 into the structure of the thin walls 28.2, 28.4, 28.5, as shown in FIGS. 46, 78, 79, 80 and 81. Thin blades 15.3*a*, 15.3*b*, 15.4, 15.5*a*, 15.5*b* (as described in FIGS. 27, 38, 81 and 82), curved blades 35*a*, 35*b* (as shown in FIGS. 34 and 35), thin hooks 21.2 (as shown in FIGS. 78 and 79), and "E"-shaped hooks 21.5 (as described in FIGS. 46 and 48) are also structurally flexible or soft; so are "T"-shaped components 39 of extension members 10 such as the one represented in FIG. 74. These thin blades and hooks may be rendered even more flexible by the configuring of notches 27, curved slits 29, circular openings 34, or slits 33 on their bone-engaging tranches 23 (as shown in FIG. 24*b*) or, in the case of the cage 1.4 represented in FIG. 35, across a substantial length of the height of the quadrilateral blades 15.4, including cutting through their corners.

Figure 75:
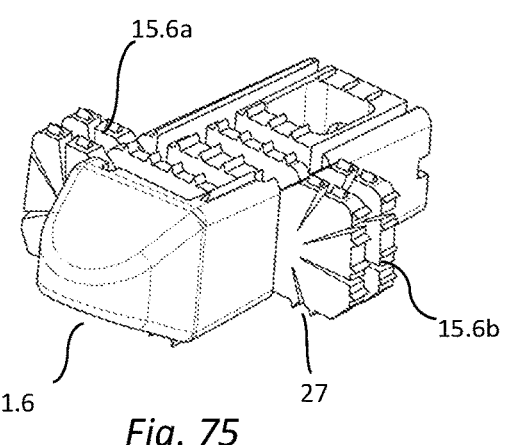
FIG. 75 represents a perspective frontal view of a variation of the cage of the sixth embodiment with deployed notched blades.
Figure 76:
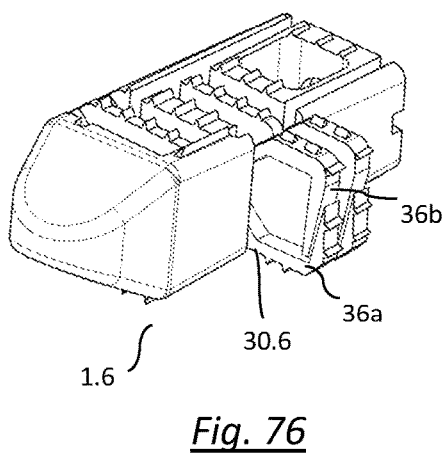
FIG. 76 represents a perspective frontal view of a variation of the cage of the sixth embodiment with deployed rings in two pincer components.
Figure 77:
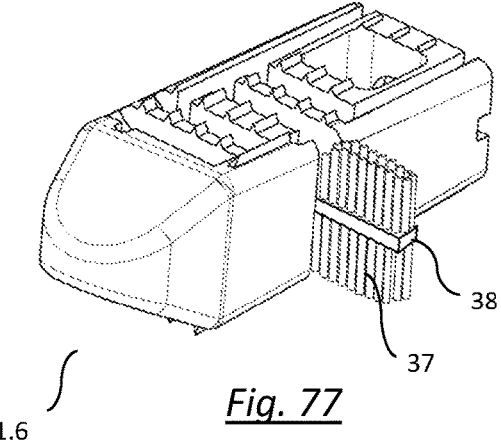
FIG. 77 represents a perspective frontal view of a variation of the cage of the sixth embodiment with a deployed extension member arranged with compacted sets of strands.

According to FIG. 75, thicker blades 15.6 such as those of the extension member 10.6 of the variation of the sixth embodiment, may also be made more flexible with flared notches 27. Thicker rings 30.6 may be configured with two pincer-components 36a, 36b such as shown in FIG. 76, to increase the dampening factor of the rings 30.6. FIG. 77 represents a variation of the cage 1.6 of the sixth embodiment with an extension member 1.6 arranged with thin compacted rods 37 mounted on a supporting structure 38 connected to the base 12.6 and deployed by the pivoting of the base 12.6: these compacted rods 37 are like the compact strands of a brush, inducing softness of the extension member 10.6 in compression and torsion of the cage 1.6.

Figure 80:
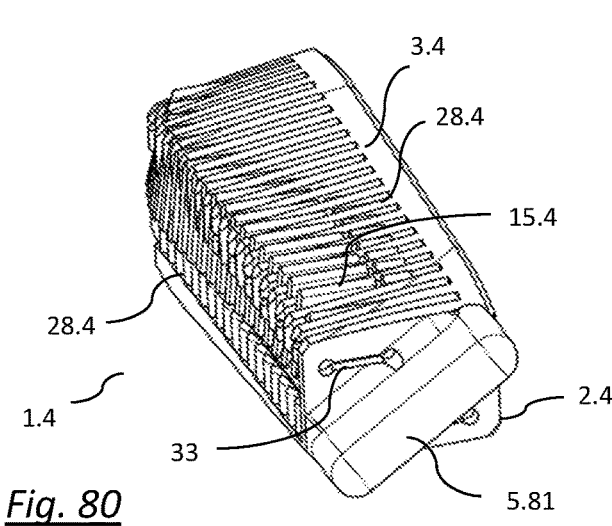
FIG. 80 represents a perspective frontal view of the cage of the fourth embodiment with oblong tip positioned obliquely in the configuration of stowed extension member.

FIGS. 80 to 83 represent a variation of the fourth embodiment, where the cage 1.4 comprises a body 2.4 configured with thin walls 28.4 and with an oblong tip 5.81 and an extension member 10.4 configured with thinner blades 15.4. The obliquely arranged oblong tip 5.81 has the same function as the oblique tip 5.81 of the eighth embodiment described in FIGS. 62 and 64, to enable an insertion of the variation of cage 1.4 according to the method described in FIGS. 37a and 37b of U.S. Ser. No. 15/739,696. The advantage of pivoting the body 2.4 in the described method is to create a buffer space on portions of the upper surface 3.4 and lower surface 4.4 of the body 2.4, which enables the cage 1.4, despite the protruding thinner blades 15.4 from the upper surface 3.4 of the body 2.4 (as shown in FIG. 80), or the thin blades 17 configured on the bone-engaging tranches 23 of the thinner blades 15.4 (as shown in FIGS. 81 and 82) to progress between the vertebrae without such protruding components engaging the vertebrae V1, V2 or hindering the progress of the cage 1.4 between the vertebrae. The other advantage of this variation, beside the dampening characteristics of the cage 1.4, is that the body 2.4 and the extension member 10.4 in the deployed configuration, define continuous and prolonged surfaces to rest against the upper and lower vertebrae V1, V2 and that such prolonged surfaces define planes which are oblique relative the longitudinal axis "α1" of the body 2.4, as shown in FIGS. 81 and 82, to restore the natural lordosis of the vertebral segment.

The flexibility of the thin walls 28, 28.2, 28.4, 28.5, of the blades 15.3a, 15.3b, 15.4, of the hooks 21.2, 21.5, and of the rings 30 may be configured to be more or less rigid on specific portions of the cage 1 by increasing the number, length, depth, thickness and angulation of notches 27 and/or slits 33 on the thin walls, or notches 27, curved slits 29 or circular openings 34 on their blades 15. They may be useful to configure cages which should be more flexible in certain of their parts and more rigid in other parts, to enable or, on the contrary, to prevent certain directional micro-movements between the two adjoining vertebrae V1, V2 of the segment.

All embodiments of the invention are configured to self-lock in their second configuration of the deployed extension member 10 by the compression force of the vertebrae V1, V2. Any suitable technical means of locking the extension member 10 into a deployed position may be applied to the invention. The Figures describe extension members 10 whose bases 12 are configured within the perimeter of the surfaces of the bodies 2 of the cages and implants 1. In different variations of the invention, the channels 14 or circular openings 11 may be configured on the body 2 beyond the lateral sides 7 of the body 2.

It goes without saying that each of the characteristics of each embodiment and any of its variations may be applied to any other embodiment or any of their variations. In variations of any embodiment, the base 12 may be angled obliquely compared to the longitudinal axes "α" or "α1" of the cage, so as to introduce differential deployment dimensions for the blades, hooks and rings which are mounted to the obliquely positioned base 12 of an extension member 10.

The bodies 2 of the cages 1 of the first to eleventh embodiments and the extension members 10 may be made in different materials.

The embodiments of the invention may apply to any implants separating and/or fusing vertebrae, whether interbody implants, vertebral body replacement implants, interspinous implants and artificial discs. The invention may also apply to the reduction and/or fusion of other bones, such as the hips, the pelvis, and any long bones and joints.

The embodiments of the invention may apply to human spinal columns and to animal spinal columns.

What is claimed is:

1. A dynamically morphing prismatic structure for use in an intervertebral bone fusion implantable device comprising:

an interlocking modular structure extending across a distal and proximal end of the device having at least one stowed structural element interconnected therewith each having a plurality of geometric shapes and openings;

the at least one stowed structural element being pivotably coupled to the interlocking modular structure to move between a stowed position, for insertion between an upper and lower vertebrae, and an unstowed position to dynamically morph the device;

an engagement element disposed at a distal end of the device;

the interlocking modular structure being operable at the proximal end by a removable instrument to advance the engagement element to increase an interstitial space between the upper and lower vertebrae to thereby deliver the device at an implant site with the device being in a compact first form factor having a first surface area in contact with the upper and lower vertebrae, and a first volume within the interstitial space;

wherein the device being configured to laterally expand by operation of the removable instrument on the interlocking modular structure and the stowed structural element, to morph from the compact first form factor to a stretched out second form factor having an increased second volume and an increased second surface area relative to the first form factor, being laterally expandable to increase interface area with the vertebrae; and wherein, the interlocking modular structure and the at least one stowed structural element being pivotably coupled to the device rotate about a central axis such that the rotation of the removable instrument at the proximal end causes the interlocking modular structure to rotate about a pivot point in a corresponding motion, and the motion of the interlocking modular structure causes the device to rotate about a range of predetermined degrees of rotation between at least two positions with respect to the upper and lower vertebrae.

2. The device according to claim 1 wherein, the interlocking modular structure being adapted to rotate about a central axis such that rotation of the removable instrument at the proximal end causes the interlocking modular structure to rotate about a pivot point which causes the device to correspondingly rotate in a first direction about a pivot point between the unstowed and stowed positions, with respect to the upper and lower vertebrae, resulting in a first orientation of the device having a separation distance between the upper and lower vertebrae larger than the interstitial space formed by the engagement element, wherein subsequent rotation by the removable instrument of the at least one stowed structural element in a second direction opposite the first direction, to thereby unstow and laterally extend the at least one stowed structural element and simultaneous continued rotation by the removable instrument of the device in the first direction result in a second orientation of the device and morph a configuration of the device into the second form factor maintaining a separation distance between the upper and lower vertebrae larger than the interstitial space formed by the engagement element.

3. The device according to claim 1 wherein, the range of predetermined degrees of rotation includes a range of about 15 degrees to 90 degrees.

4. The device according to claim 1 wherein, the interlocking modular structure includes a first plurality of surfaces in contact with the upper and lower vertebra with the device being in the first form factor, and a second plurality of surfaces in contact with the upper and lower vertebrae when the device is in its second form factor, wherein the first plurality of surfaces is dimensionally different relative to the second plurality of surfaces.

5. A dynamically morphing intervertebral bone fusion implantable device comprising:

a three dimensional generally polygonal-shaped biocompatible modular scaffold with a compact first form factor having a proximal side, a distal side, opposing sides, a top side and a bottom side, configured to define an internal compartment thereof;

an engagement element disposed at the distal side of the device;

a plurality of shaped structural elements including one of and combination of gratings, rectangular, circular, extruded interwoven holes and apertures, extending from an interior surface to an outer surface forming at least one stowable scaffold within the internal compartment, wherein the at least one stowable scaffold being pivotably coupled to the three-dimensional modular scaffold, and the structural elements being coextensive with at least one of the interior surface and outer surface of the device;

the three dimensional modular scaffold being operable by a removable instrument adapted to operate the engagement element to increase an interstitial space between an upper and lower vertebrae to thereby deliver the device at an implant site with the device being in the compact first form factor and having minimal surface contact with the upper and lower vertebrae and to rotate the device around a central axis in a first direction, such that a rotation of the removable instrument causes a corresponding motion of the three dimensional modular scaffold;

wherein, the rotation of the device by the removable instrument around the central axis in a second direction, opposite the first direction, causes the stowable scaffold to be unstowed to morph a configuration of the device into a second form factor to thereby implant the device and rest against the upper and lower vertebrae, with the second form factor providing increased surface area and volume relative to the first form factor.

6. The device according to claim 5, wherein at least one dimension of the interstitial space between the upper and lower vertebrae increases as the rotation of the removable instrument causes a corresponding motion of the three-dimensional modular scaffold.

7. The device according to claim 5, wherein at least one dimension of the interstitial space between the upper and lower vertebrae increases as the device morphs from the first form factor to the second form factor.

8. The device according to claim 5 wherein a modular scaffold geometric shape of the three dimensional generally polygonal-shaped biocompatible modular scaffold includes one of and a combination of a cube, hexahedron, octahedron, pyramid, truncated cone.

9. The device according to claim 5 wherein contact surfaces with the upper and lower vertebrae of any of the three-dimensional modular scaffold and at least one stowable scaffold differ in size between the first form factor and the second form factor.

10. The device according to claim 5 wherein the at least one stowable scaffold is actuated by a combination of rotation of the removable instrument and the device about the central axis and a compressive force generated by the vertebrae.

11. A method of implanting a dynamically morphing intervertebral bone fusion implantable device comprising the steps of:

separating an upper and lower vertebra to advance the device in an interstitial space between an upper and lower vertebra to an implant site;

inserting the device into the interstitial space in a compact first form factor configuration;

rotating the device around an axis in a first direction to enable a stowed structure to pivot laterally;

rotating the stowed structure around the axis in a second direction, opposite the first direction, to unstow the stowed structure to thereby extend laterally outward from the device to generate a second form factor configuration; and securing the unstowed structure at the implant site in the second form factor configuration to provide an increased surface area and volume within the surrounding interstitial space between the upper and lower vertebrae.

12. The method of claim 11 wherein said step of rotating the device around the axis in the first direction includes increasing the interstitial space between the upper and lower vertebrae.

13. The method of claim 11 wherein said step of rotating the stowed structure in the second direction includes increasing the interstitial space between the upper and lower vertebrae.

14. The method of claim 11 wherein said step of inserting the device includes orienting the device at an angle where rounded edges of the device slide against the upper and lower vertebrae to protect tissue damage and enable smooth deployment.

* * * * *